US011926423B2

(12) United States Patent
Hiller

(10) Patent No.: US 11,926,423 B2
(45) Date of Patent: Mar. 12, 2024

(54) AIRCRAFT AIR DUCT SYSTEM FOR PROVIDING LIGHT, DATA, ELECTRICAL POWER, AND SANITIZED AIR

(71) Applicant: The Boeing Company, Chicago, IL (US)

(72) Inventor: Nathan D. Hiller, Irvine, CA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 18/350,997

(22) Filed: Jul. 12, 2023

(65) Prior Publication Data

US 2023/0348070 A1  Nov. 2, 2023

Related U.S. Application Data

(60) Continuation-in-part of application No. 18/057,900, filed on Nov. 22, 2022, which is a division of
(Continued)

(51) Int. Cl.
*B64D 13/06* (2006.01)
*A61L 9/20* (2006.01)
(Continued)

(52) U.S. Cl.
CPC ............... *B64D 13/06* (2013.01); *A61L 9/20* (2013.01); *B60Q 3/41* (2017.02); *B64D 47/02* (2013.01);
(Continued)

(58) Field of Classification Search
CPC ... A61L 9/20; A61L 2209/12; B60Q 3/41–66; B64D 13/06; B64D 47/02;
(Continued)

(56) References Cited

U.S. PATENT DOCUMENTS 6,500,387 B1   12/2002  Bigelow
6,581,873 B2   6/2003   McDermott
(Continued)

OTHER PUBLICATIONS

United States Patent and Trademark Office. Ex Parte Quayle Action for U.S. Appl. No. 17/552,675, dated Jul. 15, 2022, pp. 1-11.
(Continued)

*Primary Examiner* — Jason M Han
(74) *Attorney, Agent, or Firm* — Vivacqua Crane PLLC

(57) ABSTRACT

An air duct system for an aircraft provides passengers with light, data, electrical power, and sanitized air. The air duct system includes an air duct having a main body and a visible light source configured to generate visible light, where the visible light is modulated by one or more controllers based on a visible light communication protocol. The air duct system simultaneously achieves four functions for improving passengers' flying experience. First, a portion of the visible light transmitted by the air duct illuminates the interior cabin of the aircraft. Second, by modulating the visible light, the air duct system transmits and distributes data that is received by the passengers' electronic devices. Third, a portion of the visible light is converted into electrical power at each passenger seat to power passengers' electronic devices. Fourth, in embodiments, the visible light is emitted at a germicidal wavelength spectrum to create sanitized air.

20 Claims, 18 Drawing Sheets

Related U.S. Application Data application No. 17/552,675, filed on Dec. 16, 2021, now Pat. No. 11,535,384, which is a division of application No. 16/782,473, filed on Feb. 5, 2020, now Pat. No. 11,230,383.

(51) Int. Cl.

| | | |
|---|---|---|
| *B60Q 3/41* | (2017.01) | |
| *B64D 47/02* | (2006.01) | |
| *F21V 7/00* | (2006.01) | |
| *F21V 9/06* | (2018.01) | |
| *F21W 106/00* | (2018.01) | |
| *F21W 107/30* | (2018.01) | |
| *F21Y 115/10* | (2016.01) | |
| *H10N 10/13* | (2023.01) | |

(52) U.S. Cl.
CPC .............. *F21V 7/0008* (2013.01); *F21V 9/06* (2013.01); *H10N 10/13* (2023.02); *A61L 2209/12* (2013.01); *B64D 2013/0644* (2013.01); *B64D 2203/00* (2013.01); *B64D 2211/00* (2013.01); *F21W 2106/00* (2018.01); *F21W 2107/30* (2018.01); *F21Y 2115/10* (2016.08)

(58) Field of Classification Search
CPC ........ B64D 2013/0644; B64D 2203/00; B64D 2211/00; F21V 7/0008; F21V 9/06; F21W 2106/00; F21W 2107/30; F21Y 2115/10; H01L 35/30; H10N 10/13; Y02T 50/40; Y02T 50/50
See application file for complete search history.

(56) References Cited

U.S. PATENT DOCUMENTS

| | | |
|---|---|---|
| 9,205,287 B2 | 12/2015 | Castanha et al. |
| 9,666,781 B2 | 5/2017 | Mitchell et al. |
| 11,230,383 B2 | 1/2022 | Hiller |
| 11,535,384 B2 | 12/2022 | Hiller |
| 11,613,362 B2 | 3/2023 | Hiller |
| 2003/0170151 A1 | 9/2003 | Hunter et al. |
| 2006/0057954 A1 | 3/2006 | Hrebeniuk |
| 2012/0168641 A1 | 7/2012 | Lizotte |
| 2012/0273340 A1 | 11/2012 | Felix |
| 2018/0313553 A1 | 11/2018 | Ma et al. |
| 2018/0356109 A1 | 12/2018 | Nomura et al. |
| 2021/0323840 A1 | 10/2021 | Lee et al. |
| 2023/0077590 A1 | 3/2023 | Hiller |

OTHER PUBLICATIONS

United States Patent and Trademark Office. Final Rejection for U.S. Appl. No. 16/782,527, dated Oct. 13, 2022, pp. 1-15.
United States Patent and Trademark Office. Non-Final Office Action for U.S. Appl. No. 16/782,527, dated Jul. 8, 2022, pp. 1-21.
United States Patent and Trademark Office. Notice of Allowance for U.S. Appl. No. 16/782,473, dated Sep. 29, 2021, pp. 1-11.
United States Patent and Trademark Office. Notice of Allowance for U.S. Appl. No. 16/782,527, dated Dec. 15, 2022, pp. 1-9.
United States Patent and Trademark Office. Notice of Allowance for U.S. Appl. No. 17/552,675, dated Aug. 29, 2022, pp. 1-11.
United States Patent and Trademark Office. Requirement for Restriction/Election for U.S. Appl. No. 16/782,473, dated Jul. 19, 2021, pp. 1-6.
United States Patent and Trademark Office. Requirement for Restriction/Election for U.S. Appl. No. 17/552,675, dated May 13, 2022, pp. 1-5.
United States Patent and Trademark Office. Non-Final Office Action for U.S. Appl. No. 18/057,900, dated Dec. 13, 2023, pp. 8-13.

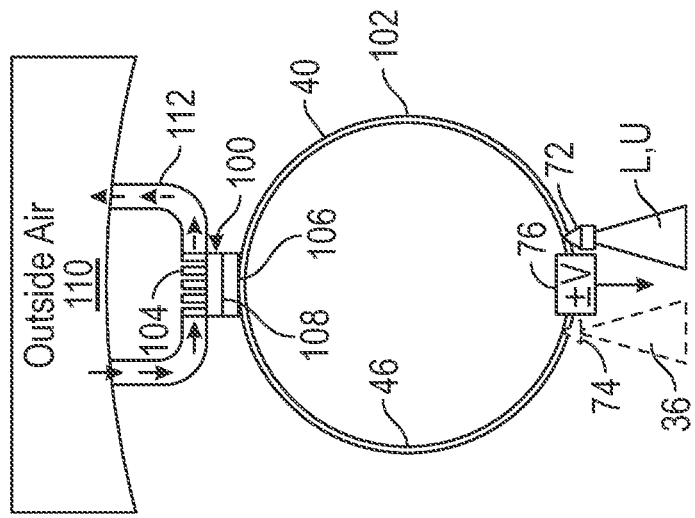
FIG. 6B Forced Convection
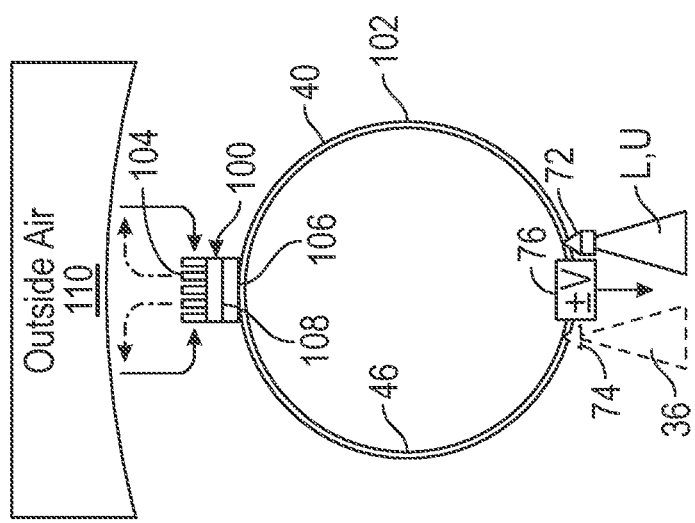
FIG. 6A Natural Convection

AIRCRAFT AIR DUCT SYSTEM FOR PROVIDING LIGHT, DATA, ELECTRICAL POWER, AND SANITIZED AIR

CROSS-REFERENCE TO RELATED APPLICATION

This application is a continuation-in-part application of U.S. application Ser. No. 18/057,900, which is a divisional application of U.S. application Ser. No. 17/552,675, filed on Dec. 16, 2021, which is a divisional application of U.S. application Ser. No. 16/782,473, filed Feb. 5, 2020. The contents of all the applications are incorporated herein by reference in their entirety.

INTRODUCTION

The present disclosure relates to an air duct system. More particularly, the present disclosure is directed towards an air duct system configured to transmit air, visible light, and data, where the data is transmitted based on a visible light communication protocol.

BACKGROUND

There is an ongoing effort to reduce the weight of an aircraft. A reduction in weight typically results in a corresponding reduction in fuel consumption of the aircraft and may also allow for an increase in payload capacity. Electrical power, current, and electronic signals are typically conducted through wires or cables constructed of copper or aluminum as the conductive medium. For example, wiring is used in the passenger cabin of the aircraft to power various electronic devices such as, for example, overheard lighting and displays. However, wiring contributes significantly to the total weight of the aircraft.

SUMMARY

According to several aspects, an air duct system is disclosed, and includes air duct having a main body. The main body of the air duct defines a passageway having a reflective inner surface. The air duct system also includes a visible light source configured to generate visible light, where the visible light source directs the visible light along the reflective inner surface of the air duct. The air duct system also includes one or more control modules in electronic communication with the visible light source, where the one or more control modules instruct the visible light source to modulate the visible light based on a visible light communication protocol, and wherein the visible light is a medium for transmitting data.

In another aspect, an aircraft is disclosed, and includes an air duct system. The air duct system includes an air duct having a main body, where the main body of the air duct defines a passageway having a reflective inner surface. The air duct system includes a visible light source configured to generate visible light, where the visible light source directs the visible light along the reflective inner surface of the air duct. The air duct system includes one or more control modules in electronic communication with the visible light source, where the one or more control modules instruct the visible light source to modulate the visible light based on a visible light communication protocol, and the visible light is a medium for transmitting data. The air duct system also includes one or more light-transmitting elements, where each light-transmitting element is placed within a corresponding aperture disposed along the main body of the air duct, and a first portion of the visible light exits the air duct through one of the corresponding apertures to provide the data. The air duct system also includes one or more photovoltaic devices disposed along the reflective inner surface of the air duct. The air duct system also includes one or more corresponding electronic devices that are each electrically connected to one of the one or more photovoltaic devices, where a second portion of the visible light impinges against one of the one or more photovoltaic devices and is converted into electrical power provided to one of the corresponding electronic devices.

In still another aspect, a method for transmitting air, visible light, and data through an air duct of an aircraft is disclosed. The method includes receiving, by the air duct, conditioned air and visible light, where a visible light source is modulated based on a visible light communication protocol by one or more control modules to generate the visible light. The method includes directing the visible light along a reflective inner surface of the air duct, where the visible light reflects off the reflective inner surface and travels along a passageway of the air duct. The method also includes allowing a portion of the visible light generated by the visible light source to exit the air duct through one or more lighting apertures disposed along a main body of the air duct.

The features, functions, and advantages that have been discussed may be achieved independently in various embodiments or may be combined in other embodiments. Further details of which can be seen with reference to the follo wing description and drawings.

BRIEF DESCRIPTION OF THE DRAWINGS

The drawings described herein are for illustration purposes only and are not intended to limit the scope of the present disclosure in any way.

FIG. 6A illustrates a thermoelectric generator disposed along an outer surface of the air duct, where the thermoelectrical generator cooled by natural convection, according to an exemplary embodiment;

FIG. 6B illustrates the thermoelectric generator in FIG. 6A cooled by forced convection, according to an exemplary embodiment;

DETAILED DESCRIPTION

The present disclosure is directed towards an air duct system configured to transmit air, visible light, and data to passengers in a vehicle, such as an aircraft. The air duct system includes an air duct having a main body, a visible light source, and one or more control modules configured to generate visible light. The main body of the air duct defines a passageway having a reflective inner surface. The visible light source is configured to generate visible light and directs the visible light along the reflective inner surface of the air duct. The one or more control modules instructs the visible light source to modulate the visible light based on a visible light communication protocol. Accordingly, the disclosed air duct system transmits data without utilizing wiring or cables, and results in a significant reduction in weight.

The following description is merely exemplary in nature and is not intended to limit the present disclosure, application, or uses.

Figure 1:
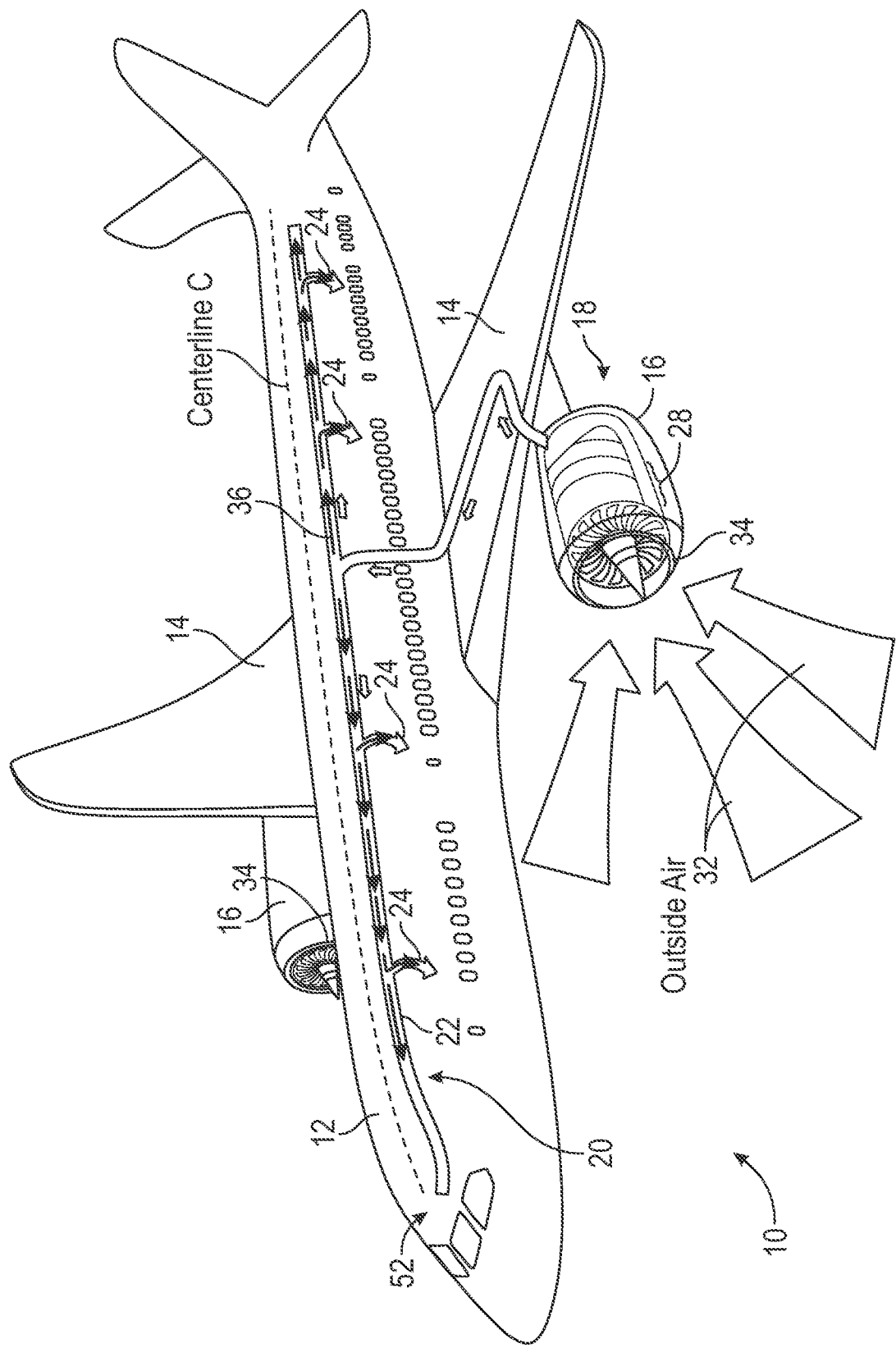
FIG. 1 is a perspective, partially sectioned view of an aircraft with the disclosed air duct system, according to an exemplary embodiment.

Referring to FIG. 1, a partially cross-sectioned aircraft 10 is shown. The aircraft 10 includes a fuselage 12, a pair of wings 14, a nacelle 16 mounted to each wing 14, a main engine 18 housed within each nacelle 16 (only one of the main engines 18 are shown), and an air duct system 20. The air duct system 20 includes an overhead air duct 22 and a plurality of distribution ducts 24. Outside air 32 enters the main engine 18 through an inlet 34 and is compressed and heated by a compressor section 28 of the main engine 18 into heated pressurized air. A portion of the heated pressurized air from the compressor sections 28 of the main engine 18, which is referred to as bleed air, is cooled and then remixed with recirculated air to create conditioned air 36. The conditioned air 36 is set to a predetermined temperature. The conditioned air 36 flows through the overhead air duct 22, to the distribution ducts 24, and is delivered throughout an interior cabin 58 (FIG. 2) of the aircraft 10.

In the non-limiting embodiment as shown in FIG. 1, the overhead air duct 22 is linear and extends along a centerline C of the aircraft 10. However, it is to be appreciated that the overhead air duct 22 may include a non-linear or curved profile as well. Moreover, although the figures illustrate the disclosed air duct system 20 as part of an aircraft, the air duct system 20 may be used in other applications as well.

Figure 2:
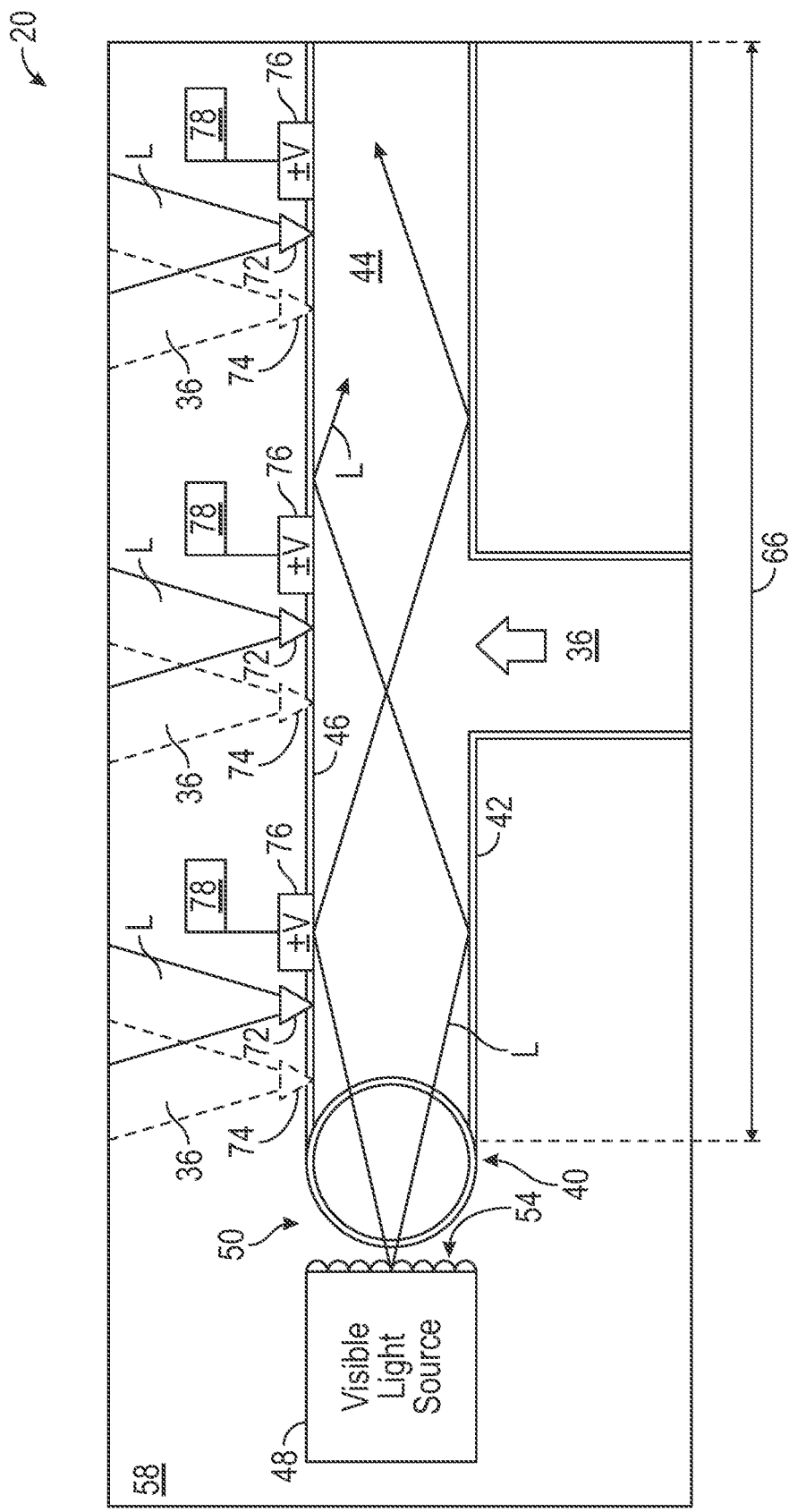
FIG. 2 is a schematic diagram of the air duct system including a visible light source and one or more photovoltaic devices configured to transform visible light into electrical power, according to an exemplary embodiment.

FIG. 2 is a schematic diagram of an embodiment of the air duct system 20 for transmitting visible light L and electrical energy. As explained below, the disclosed air duct system 20 is configured to transmit air, visible light, and electrical power. Specifically, a portion of the visible light L is transformed into electrical power. In another embodiment, the disclosed air duct system 20 includes an ultraviolet light source 30 (seen in FIG. 7) that exposes the conditioned air 36 flowing through the overhead air duct 22 to ultraviolet light. The ultraviolet light emitted by the ultraviolet light source 30 is of a frequency or intensity sufficient to sanitize air.

Turning back to FIG. 2, the air duct system 20 includes an air duct 40 having a main body 42. The main body 42 of the air duct 40 defines a passageway 44 having a reflective inner surface 46, where the conditioned air 36 and the visible light L are transmitted through the passageway 44. The reflective inner surface 46 of the main body 42 of the air duct 40 includes a reflectance of at least fifty percent. For example, an aluminum coating would provide a reflectance of at least fifty percent. However, in an embodiment the reflective inner surface 46 of the main body of the air duct 40 includes a reflectance of at least ninety-nine percent. One example of a material for coating the reflective inner surface 46 of the air duct 40 that has a reflectance of at least ninety-nine percent is a reflective film. In an embodiment, the reflective film is applied to the air duct 40 during fabrication. In an alternative embodiment, a conventional air duct system is retrofitted by applying the reflective film to the inner surface of the conventional air duct. One commercially available example of a reflective film is Specular Film DF2000MA, which is available from the 3M Company of Maplewood, MN. In another embodiment, the reflective inner surface 46 is coated with an optical supermirror, a Bragg grating, photonic crystal, or a nanostructured materials. A Bragg grating is a reflecting structure having a periodic refractive index modulation.

The air duct system 20 also includes a visible light source 48 configured to generate the visible light L, where the visible light source 48 directs the visible light L along the reflective inner surface 46 of the air duct 40. The visible light L then impinges against the reflective inner surface 46 and travels along the passageway 44 of the air duct 40. In one embodiment, the visible light source 48 is positioned at an end 50 of the air duct 40 situated at the front end 52 of the aircraft 10 (FIG. 1). However, it is to be appreciated that the position of the visible light source 48 is not limited to this configuration as long as the visible light L is directed towards the reflective inner surface 46 of the air duct 40 and is transmitted along a length 66 of the air duct 40. In one non-limiting embodiment, the visible light source 48 includes an array of light-emitting diodes (LEDs) 54. In an embodiment, the LEDs 54 emit white light at ten kilowatts, however, it is to be appreciated that other types of devices that emit visible light may be used as well. Furthermore, it is also to be appreciated that the visible light L is not limited to only white light. Instead, the visible light L may be of any color and intensity that is required for a particular application.

Figure 3:
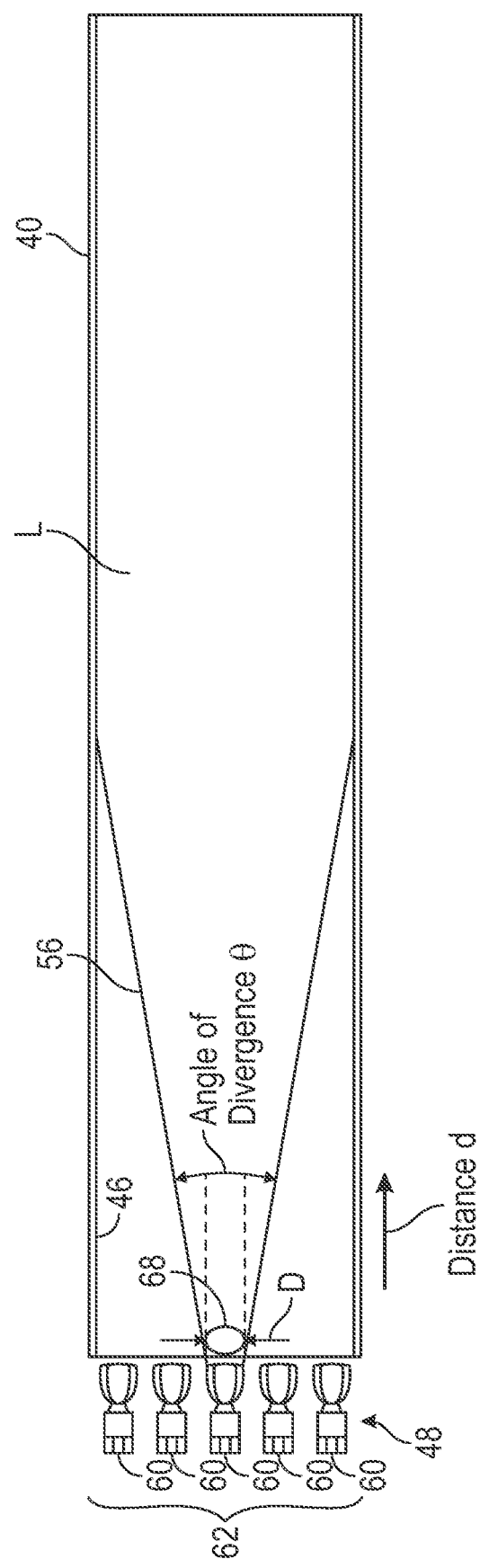
FIG. 3 is a schematic diagram of a single beam of visible light being transmitted by the visible light source, according to an exemplary embodiment.

FIG. 3 is an illustration of a light beam 56 emitted from a lamp 60. The lamp 60 is part of an array 62 of lamps 60 that are the visible light source 48. For purposes of clarity, only one of lamps 60 is emitting visible light L in FIG. 3. In an embodiment, the lamps 60 are parabolic aluminized reflector lamps, however, it is to be appreciated that other types of lamps may be used as well. The light beam 56 is semi-culminated, which means that the light beam 56 emitted from the visible light source 48 (i.e., the lamps 60) has an angle of divergence θ of ten degrees or less. The angle of divergence θ represents the amount of angular spread that the light beam 56 undergoes as the distance d from the visible light source 48 increases. As seen in FIG. 3, the light beam 56 diverges away from a center diameter D, where the center diameter D represents a maximum intensity 68 of the light beam 56. The light beam 56 is semi-culminated so as to direct the visible light L along the reflective inner surface 46 of the air duct 40.

Referring back to FIG. 2, the air duct system 20 further includes one or more of lighting apertures 72 disposed along the main body 42 of the air duct 40, where a portion of the visible light L generated by the visible light source 48 exits the air duct 40 through the lighting apertures 72. The lighting apertures 72 each represent the overhead light for a passenger located within the interior cabin 58 of the aircraft 10 (FIG. 1). Accordingly, the lighting apertures 72 replace a traditional lamp that is used to provide visible light to a passenger. The lighting apertures 72 also eliminate the need to route wiring or cables through the air duct 40 as well, which in turn reduces weight in the aircraft 10. The air duct 40 further includes one or more air valves 74 disposed along the main body 42 of the air duct 40. The air valves 74 are each configured to release the conditioned air 36 (FIG. 1) that travels through the air duct system 20.

Continuing to refer to FIG. 2, the air duct system 20 also includes one or more photovoltaic devices 76 that are disposed along the reflective inner surface 46 of the air duct 40. A portion of the visible light L generated by the visible light source 48 impinges against each photovoltaic device 76 and is then converted into electrical power by the photovoltaic devices 76. In the embodiment as shown, each photovoltaic device 76 provides electrical power to a corresponding electronic device 78. In an embodiment, an individual electronic device 78 is provided for each passenger in the aircraft 10. For example, in one embodiment, the electronic device 78 is a television display that is provided to each passenger seated within the interior cabin 58 of the aircraft 10. Some examples of photovoltaic devices 76 include, but are not limited to, crystalline silicon photovoltaic devices having an efficiency of about 25%, multi-junction photovoltaic devices having an efficiency of about 45%, and perovskite photovoltaic devices. Since the silicon photovoltaic devices produce less electrical power, they may be used in lower-cost application.

As seen in FIG. 2, a single lighting aperture 72, a single air valve 74, a single photovoltaic device 76, and a single electronic device 78 are provided for each passenger of the aircraft 10. However, in another embodiment, the power from multiple photovoltaic devices 76 are combined together to provide power to a single electronic device 78 requiring more electrical energy than a single electronic device allotted to a passenger, such as a television screen. For example, in another embodiment, the power generated from a plurality of the photovoltaic devices 76 are combined together to provide power to an electronic device such as a microwave.

Figure 4:
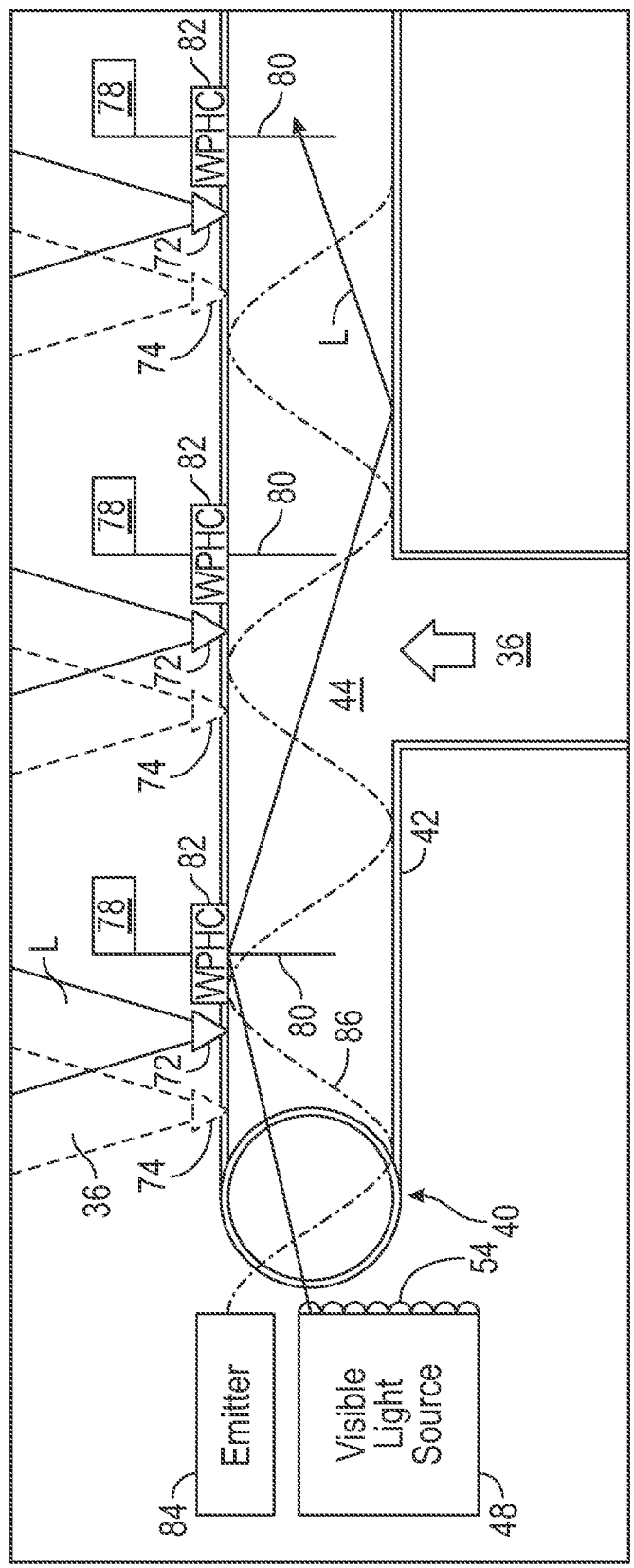
FIG. 4 is an alternative embodiment of the air duct system in FIG. 2 having a radio frequency emitter, one or more antennas, and one or more power harvesting circuits, according to an exemplary embodiment.

Although FIG. 2 illustrates photovoltaic devices 76 for transforming the visible light L into electrical energy, in one embodiment the photovoltaic devices 76 are omitted. Instead, as shown in FIG. 4, the photovoltaic devices 76 are replaced by an antenna 80 and a power harvesting circuit 82. In the embodiment as shown in FIG. 4, the air duct system 20 further includes an emitter 84 configured to emit radio frequency waves 86. The emitter 84 directs the radio frequency waves 86 along the reflective inner surface 46 of the air duct 40. The radio frequency waves 86 impinge against the reflective inner surface 46 of the air duct 40 and are intercepted by one of the antennas 80. It is to be appreciated that the reflective inner surface 46 of the air duct 40 reflects the radio frequency waves 86. Therefore, the radio frequency waves 86 travel through the air duct 40 and are not transmitted to other surrounding components of the aircraft 10. As seen in FIG. 4, the antennas 80 each extend partially into the passageway 44 of the air duct 40. Therefore, the antennas 80 are each positioned to intercept the radio frequency waves 86 that travel through the air duct 40.

Figure 5:
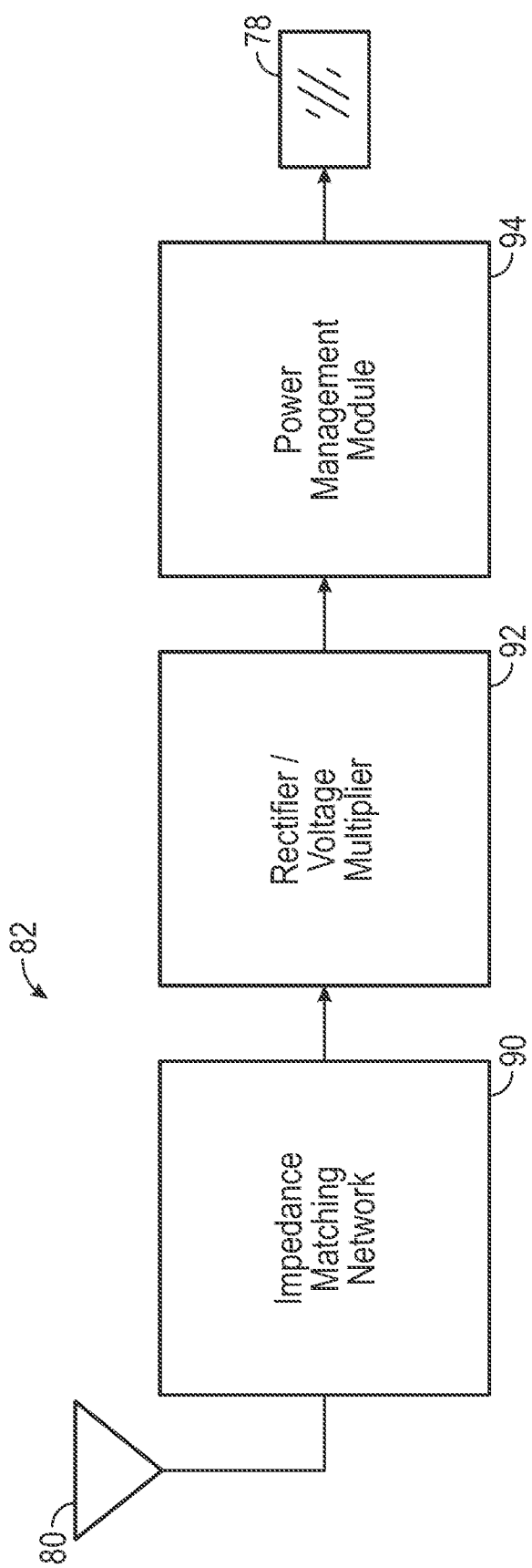
FIG. 5 is a schematic diagram of the power harvesting circuit shown in FIG. 4, according to an exemplary embodiment.

The antennas 80 are each connected to a corresponding power harvesting circuit 82, where the radio frequency waves 86 are received by the antennas 80 and are converted into electrical power by the corresponding power harvesting circuits 82. FIG. 5 is a schematic diagram illustrating an embodiment of the power harvesting circuit 82. In the embodiment as shown in FIG. 5, the power harvesting circuit 82 includes an impedance matching network 90, a combined rectifier and voltage multiplier 92, and a power management module 94. The impedance matching network 90 is configured to transform the impedance of the antenna 80 into a transmission impedance of the power harvesting circuit 82. The combined rectifier and voltage multiplier 92 is configured to convert the radio frequency waves 86 into DC power, which provides the voltage required by the electronic devices 78. The power management module 94 stores the electrical energy and provides the electrical energy to the corresponding electronic device 78. Turning back to FIG. 4, it is to be appreciated that since the visible light source 48 is not used to transmit electrical energy, the visible light L may be less intense when compared to a visible light source 48 for transmitting both electrical power and visible light.

FIGS. 6A-6D illustrate yet another embodiment of the air duct system 20 including one or more thermoelectric generators 100 disposed along an outer surface 102 of the air duct 40. It is to be appreciated that heat is generated as the visible light L impinges against the reflective inner surface 46 of the air duct 40. Heat is also produced when the radio frequency waves 86 (seen in FIG. 4) or the ultraviolet light U (seen in FIG. 7) impinges against the reflective inner surface 46 of the air duct 40 as well. The thermoelectric generator 100 is configured to transform the heat into electrical energy that may be used by one or more systems in the aircraft 10. The thermoelectric generator 100 is a thermoelectric module, such as a solid-state thermoelectric module.

Figure 6D:
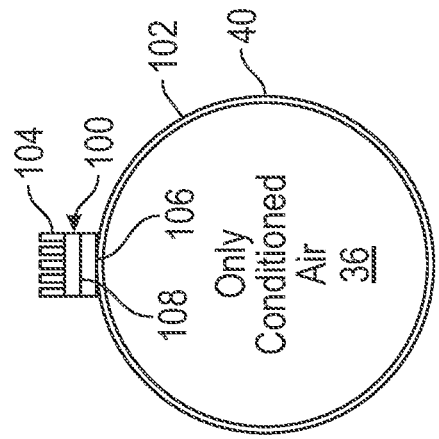
FIG. 6D illustrates the thermoelectric generator disposed along another embodiment of the air duct only transmitting the conditioned air, according to an exemplary embodiment.
Figure 6C:
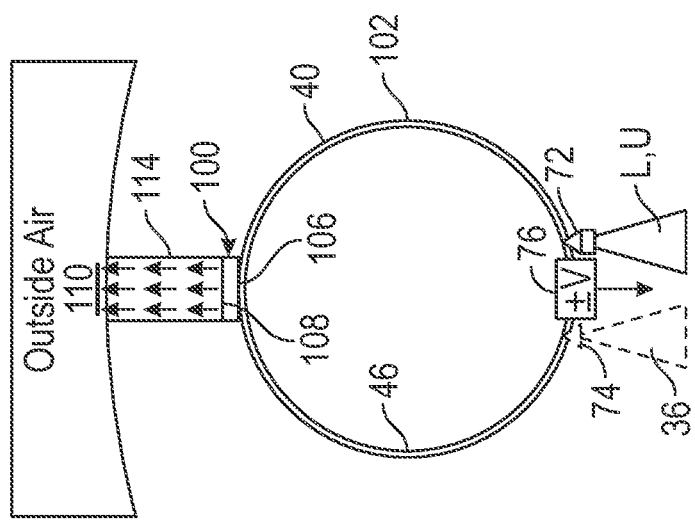
FIG. 6C illustrates the thermoelectric generator cooled by conduction, according to an exemplary embodiment.

The thermoelectric generator 100 includes a heat sink 104 (in the embodiment as shown in FIG. 6C, the heat sink 104 is omitted). The thermoelectric generator 100 also includes a hot side 106 and a cold side 108. The hot side 106 of the thermoelectric generator 100 is positioned along the outer surface 102 of the air duct 40. In an embodiment, the thermoelectric generator 100 is physically attached to outer surface 102 of the air duct 40 by adhesives or mechanical attachments such as screws or brackets (not shown). The cold side 108 of the thermoelectric generator 100 opposes the hot side 106 of the thermoelectric generator 100 and contacts the heat sink 104. It is to be appreciated that the terms hot and cold are intended to describe relative temperatures of the thermoelectric generator 100. Consequently, when the outer surface 102 of the air duct heats the hot side 106 of the thermoelectric generator 100 to a temperature greater than the cold side 108 an electric current is produced.

The thermoelectric generator 100 is cooled by natural convection, forced convection, or solid conduction. In the embodiment as shown in FIG. 6A, the thermoelectric generator 100 is cooled using natural convention. Specifically, outside air 110 (which is relatively cold) flows over the heat sink 104 of the thermoelectric generator 100. In the embodiment as shown in FIG. 6B, the thermoelectric generator 100 is cooled using forced convention. Specifically, the outside air 110 is channeled over the heat sink 104 of the thermoelectric generator 100 by a tube 112. In the embodiment as shown in FIG. 6C, the thermoelectric generator 100 is cooled using solid conduction. Specifically, a solid 114 having a high thermal conductivity is used to connect the cold side 108 of the thermoelectric generator 100 with the outside air 110. Some examples of solids having a high thermal conductivity include, but are not limited to, aluminum, graphene, and single wall carbon nanotubes. In another embodiment, the solid 114 is a heat pipe. A heat pipe is a two phase heat transfer device including an envelope, a working fluid, and a wick structure.

Turning now to FIG. 6D, in another embodiment the air duct 40 does not include the ultraviolet light source 30 (FIG. 7), the visible light source 48 (FIG. 2), or the emitter 84 (FIG. 4). Instead, the air duct 40 transmits the conditioned air 36. However, the outer surface 102 is still heated to a temperature that is greater than the outside air 110. Thus, a temperature differential still exists between the hot side 106 and the cold side 108 of the thermoelectric generator 100 sufficient to generate electric current.

Figure 7:
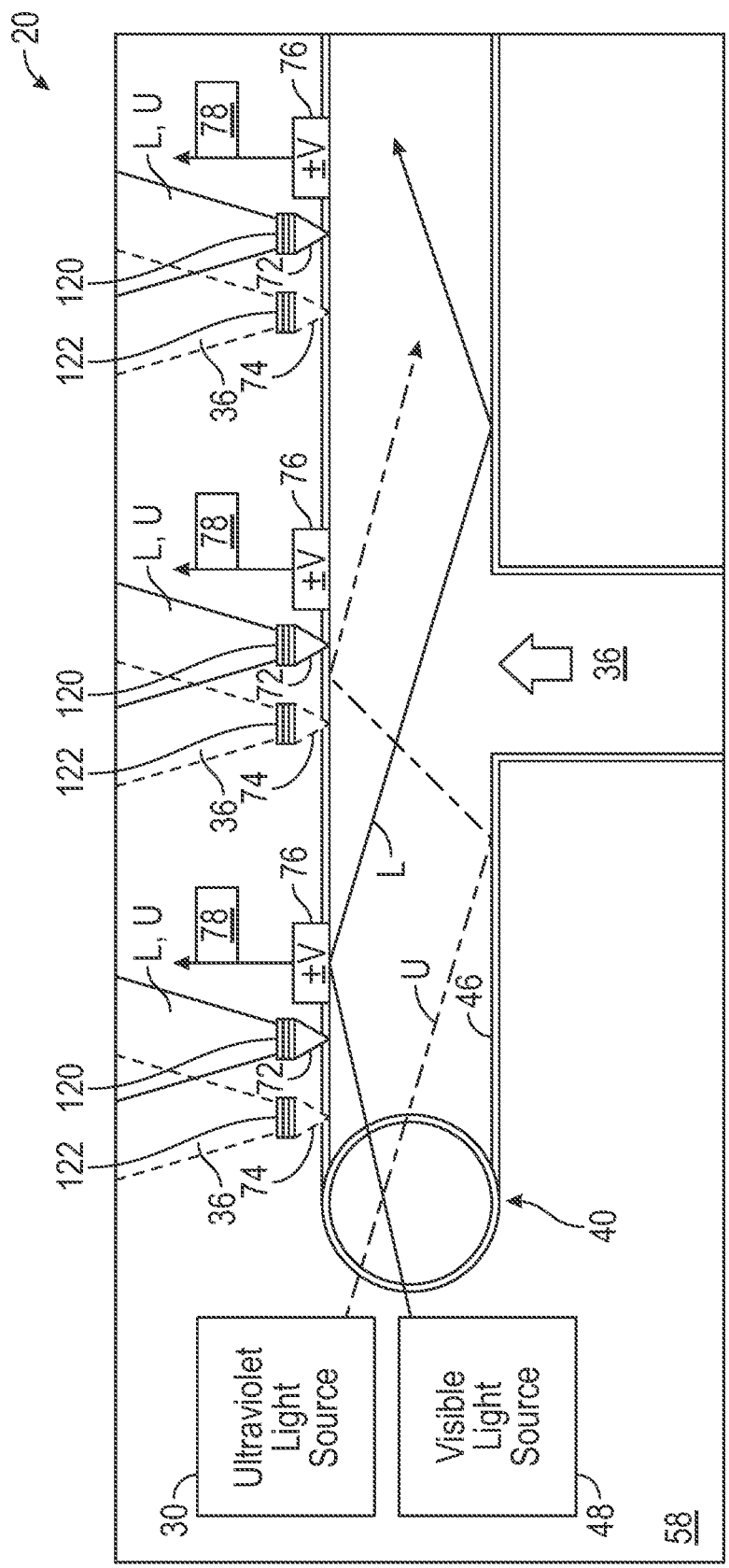
FIG. 7 is another embodiment of the air duct system shown in FIG. 2 further including an ultraviolet light source, according to an exemplary embodiment.

FIG. 7 illustrates yet another embodiment of the air duct 40 including the ultraviolet light source 30 configured to generate the ultraviolet light U. The source of ultraviolet light source 30 may be, for example, an ultraviolet laser or a low-pressure ultraviolet lamp. The ultraviolet light source 30 directs the ultraviolet light U along the reflective inner surface 46 of the air duct 40, where the ultraviolet light U sanitizes the conditioned air 36 flowing through the overhead air duct 22 is sanitized. In other words, the ultraviolet light U kills airborne germs, bacteria, and other contaminates that are suspended within the conditioned air 36 that flows through the air duct 40. The ultraviolet light U includes a germicidal wavelength ranging from 185 to 400 nanometers (nm). The germicidal wavelength range includes near ultraviolet wavelengths of about 220 nm to about 400 nm and far ultraviolet wavelengths of about 190 nm to about 220 nm. The power of the ultraviolet light source 30 may vary based on the size of the air duct 40, airflow rate, and the power of the ultraviolet light source 30, and in one embodiment may range from 100 Watts to 1 Kilowatt.

Continuing to refer to FIG. 7, the air duct system 20 further includes a plurality of ultraviolet optical filters 120 placed over each of the plurality of lighting apertures 72. The ultraviolet optical filters 120 allows for the visible light L to enter the interior cabin 58 and at the same time filters the ultraviolet light U. This is to prevent ultraviolet light expose to the passengers located in the interior cabin 58 of the aircraft 10. The air duct system 20 also includes a plurality of ultraviolet optical filters 122 placed over each of the plurality of air valves 74 as well. The ultraviolet optical filters 122 are configured to allows for the conditioned air 36 to flow to the interior cabin 58. In an embodiment, the ultraviolet optical filters 120, 122 are constructed of a glass that is opaque to wavelengths in the germicidal wavelength.

Figure 8:
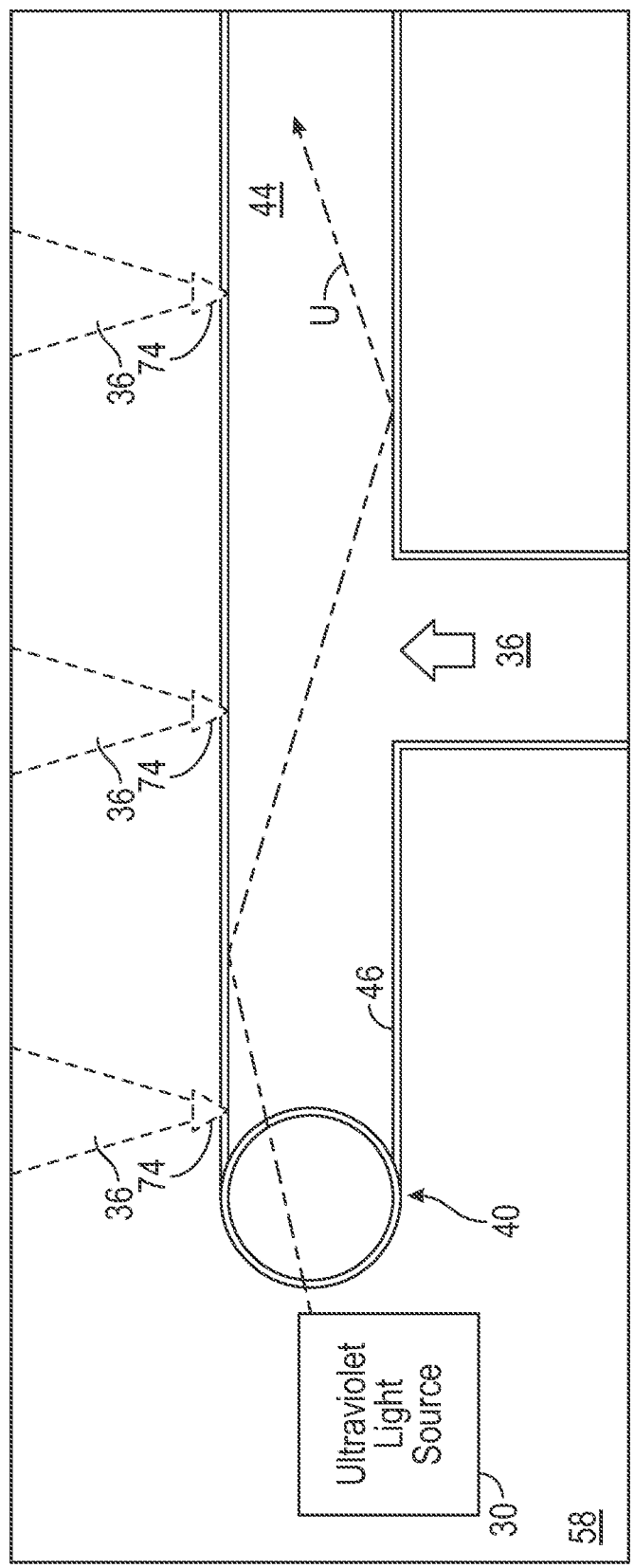
FIG. 8 is a schematic diagram of another embodiment of the air duct system including only the ultraviolet light source, according to an exemplary embodiment.

Although FIG. 7 illustrates both the ultraviolet light source 30 and the visible light source 48, in another embodiment the ultraviolet light source 30 is used alone. Referring now to FIG. 8, the air duct system 20 includes only the ultraviolet light source 30 to sanitize the conditioned air 36. Since the air duct system 20 in FIG. 8 does not transmit visible light, the reflective inner surface 46 does not require a relatively high reflectance that is described above (i.e., a reflectance of ninety-nine percent). Instead, the reflective inner surface 46 of the main body 42 of the air duct 40 includes a reflectance of at least twenty-five percent.

Figure 9:
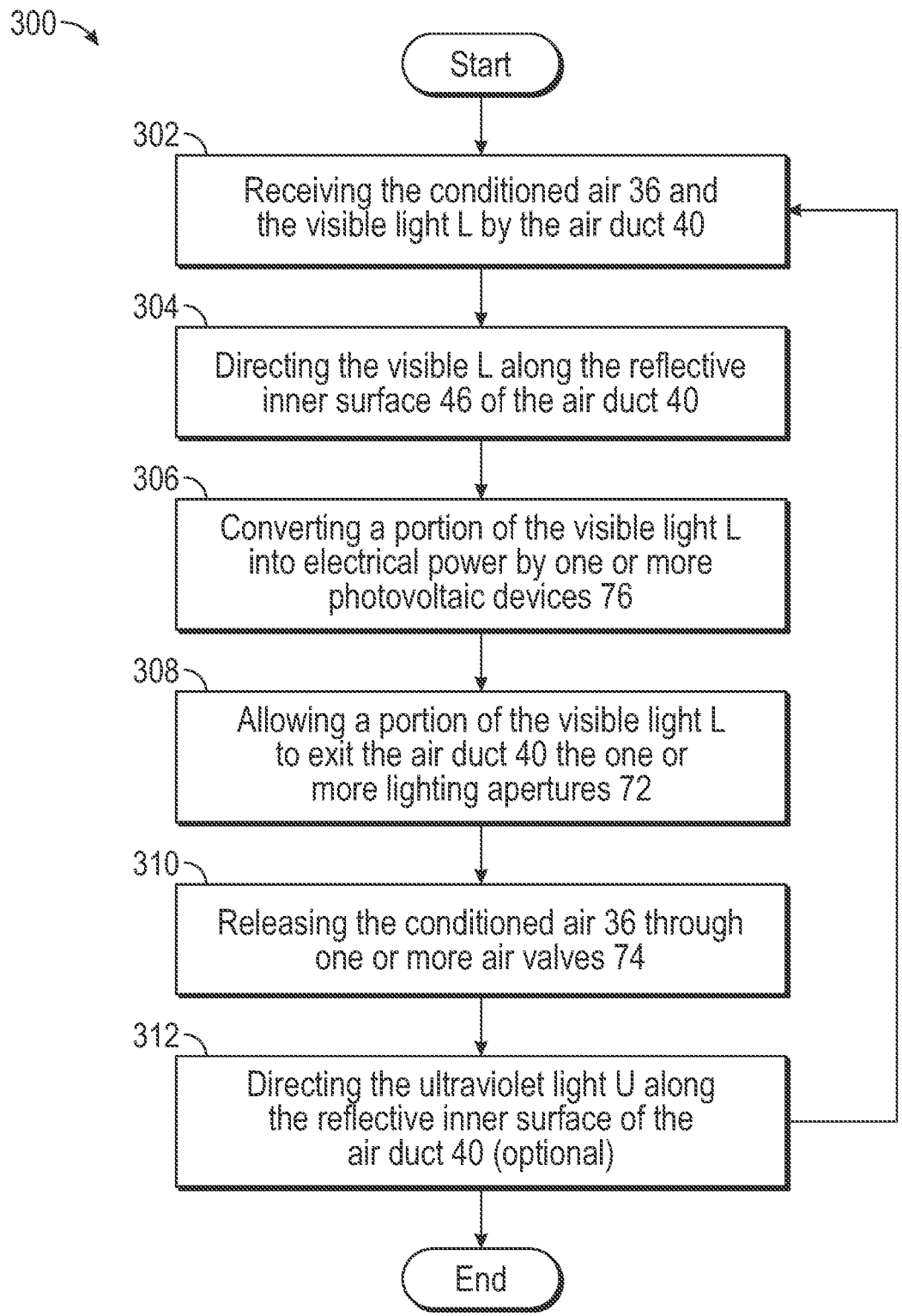
FIG. 9 is a process flow diagram illustrating a method for transmitting air, visible light, and electrical power by the disclosed air duct, according to an exemplary embodiment.

FIG. 9 is an exemplary process flow diagram illustrating a method 300 transmitting air, visible light, and electrical power through the air duct 40 of the aircraft 10. Referring to FIGS. 1, 2, and 9, the method 300 begins at block 302. In block 302, the air duct 40 receives the conditioned air 36 and visible light L. As mentioned above, the visible light L is generated by the visible light source 48. The method 300 may then proceed to block 304.

In block 304, the visible light L is directed along the reflective inner surface 46 of the air duct 40, where the visible light L reflects off of the reflective inner surface 46 and travels along the passageway 44 of the air duct 40. The method 300 may then proceed to block 306.

In block 306, a portion of the visible light L is converted into electrical power by one or more photovoltaic devices 76 disposed along the reflective inner surface 46 of the air duct 40. As mentioned above, the photovoltaic device 76 provides electrical power to a corresponding electronic device 78. The method 300 may then proceed to block 308.

In block 308, a portion of the visible light L is allowed to exit the air duct 40 through one or more lighting apertures 72 disposed along the main body 42 of the air duct 40. The method 300 may then proceed to block 310.

In block 310, the conditioned air 36 is released by one or more air valves 74 disposed along the main body 42 of the air duct 40. The method 300 may then proceed to block 312.

It is to be appreciated that block 312 is optional and may be omitted in some instances. In block 312, the ultraviolet light U (seen in FIG. 7) is directed along the reflective inner surface 46 of the air duct 40. As mentioned above, the ultraviolet light U includes a germicidal wavelength ranging from 185 to 400 nanometers. The method 300 may then terminate or, alternatively, proceed back to block 302.

Referring to FIGS. 1-7 and 9, the disclosed air duct system is configured to provide conditioned air, visible light, and electrical power. The electrical power is transmitted through the air duct in the form of visible light and is transformed into electrical power by photovoltaic devices. As a result, there is no wiring or cables to transmit electrical power to the overhead lights in an aircraft. Moreover, the photovoltaic devices provide electrical power to other electronic devices, such as individual television screens for each passenger. Accordingly, there is no wiring or cables included for transmitting electrical power to various electronic devices in the aircraft. This results in a significant weight savings, which in turn enhances fuel efficiency.

Figure 10:
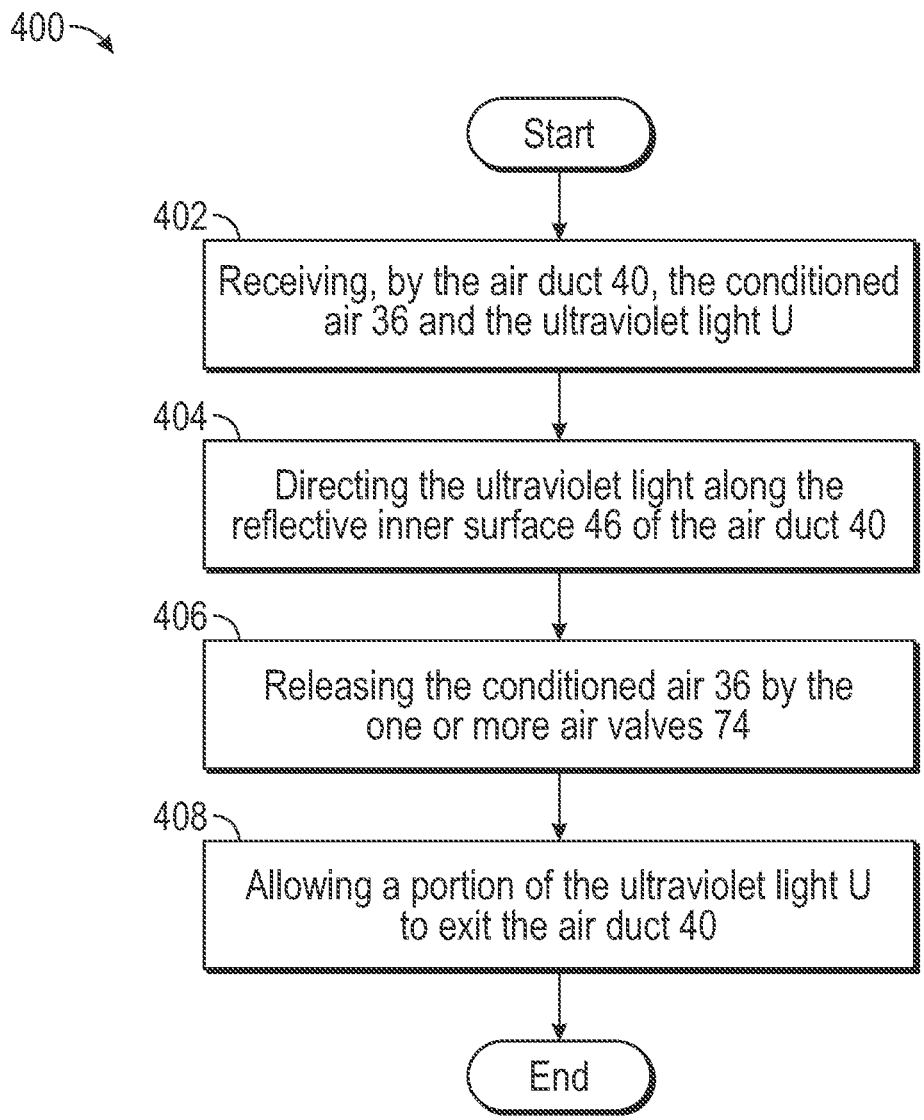
FIG. 10 is a process flow diagram illustrating a method for sanitizing air flowing through the disclosed air duct, according to an exemplary embodiment.

As mentioned above, in the embodiment as shown in FIG. 8, the ultraviolet light source 30 is used alone (i.e., without the visible light source 48). Turning now to FIG. 10, a process flow diagram illustrating a method 400 for sanitizing the conditioned air 36 in an aircraft 10. Referring now to FIGS. 8 and 10, the method 400 begins at block 402. In block 402, the air duct 40 receives the conditioned air 36 and ultraviolet light U. As mentioned above, the visible light L is generated by the ultraviolet light source 30. The method 300 may then proceed to block 404.

In block 404, the ultraviolet light U is directed along the reflective inner surface 46 of the air duct 40, where the ultraviolet light U reflects off of the reflective inner surface 46 and travels along the passageway 44 of the air duct 40, and sanitizes the conditioned air 36 flowing through the air duct 40. The method 300 may then proceed to block 406.

In block 406, the conditioned air 36 is released by one or more air valves 74 disposed along the main body 42 of the air duct 40. As mentioned above, the ultraviolet optical filters 122 is placed over the air valves 74 to prevent the transmission of the ultraviolet light U. The method 400 may then proceed to block 408.

In block 408, a portion of the ultraviolet light U is allowed to exit the air duct 40 through one or more lighting apertures 72 disposed along the main body 42 of the air duct 40. As mentioned above, a plurality of ultraviolet optical filters 120 are placed over the lighting apertures 72 to prevent the ultraviolet light U from traveling into the interior cabin 58 of the aircraft 10. The method 400 may then proceed terminate or proceed back to block 402.

Referring to FIGS. 8 and 10, the disclosed air duct system provides a lightweight approach for sanitizing the conditioned air throughout the interior cabin of an aircraft. This in turn prevents the transmission of infectious diseases that may occur among air travelers. In an embodiment, the ultraviolet light may kill some types of serious infectious diseases as well.

Figure 11:
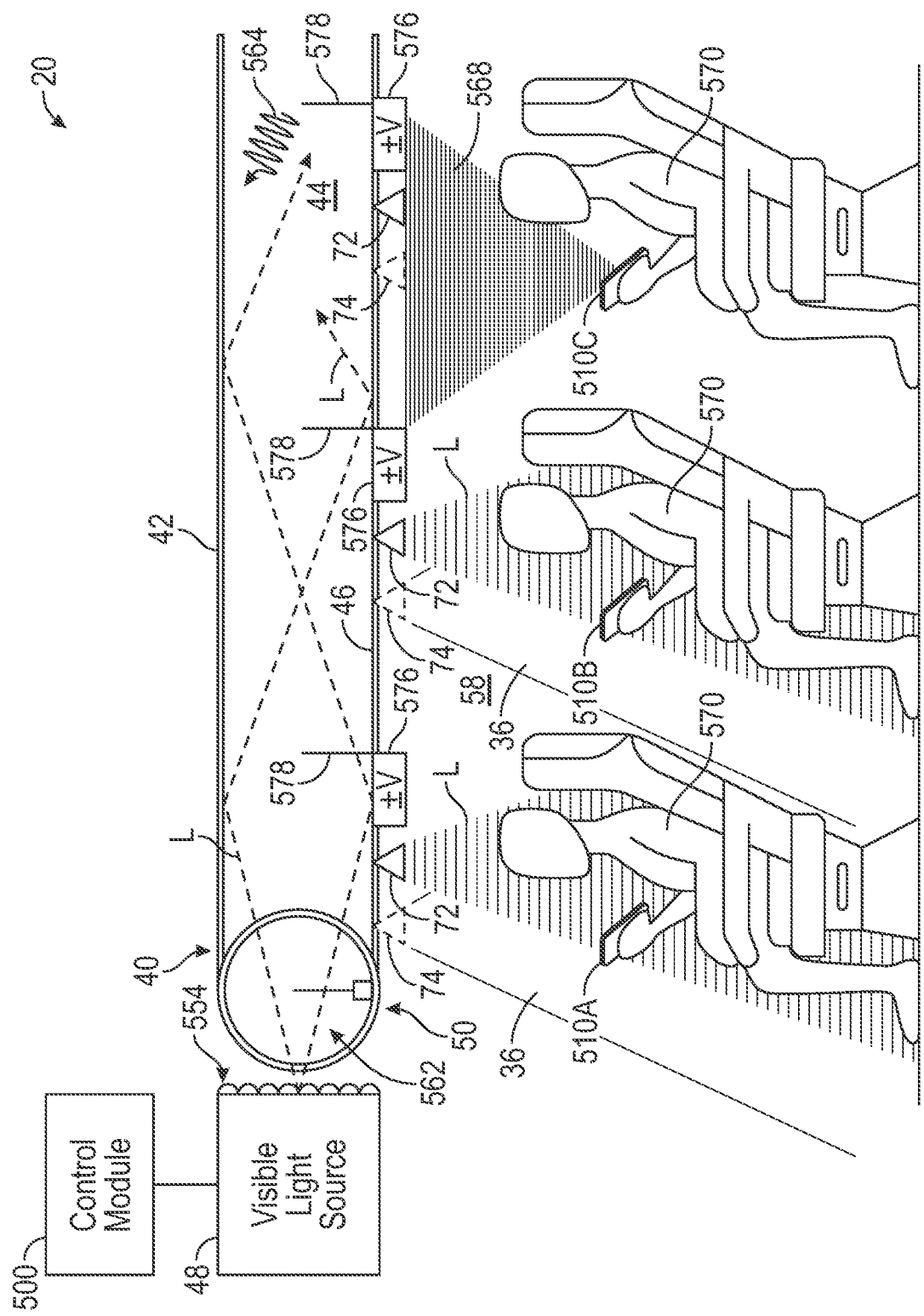
FIG. 11 is a schematic diagram of yet another embodiment of the air duct system that transmits visible light and data, where the data is received by one or more electronic devices, according to an exemplary embodiment.

FIG. 11 is a schematic diagram of another embodiment of the air duct system 20 for transmitting the visible light L and data. As explained below, the disclosed air duct system 20 is configured to transmit air, visible light, and data. Specifically, the visible light L emitted by the visible light source 48 is modulated based on a visible light communication (VLC) protocol by one or more control modules 500. As seen in FIG. 11, The one or more control modules 500 are in electronic communication with the visible light source 48. The one or more control modules 500 instruct the visible light source 48 to modulate the visible light L based on a visible light communication protocol, where the visible light L is a medium for transmitting the data. In one non-limiting embodiment, the visible light L is modulated based on the light fidelity (Li-Fi) standard as set forth by the Institute of Electrical and Electronics Engineers (IEEE) 802.11 family of standards, however, it is to be appreciated that other visible light communication protocols may be used as well.

It is to be appreciated that the one or more control modules 500 modulate the visible light L generated by the visible light source 48 based on one or more of the following modulation techniques: frequency modulation, intensity modulation, and polarization modulation. It is to be appreciated that in embodiments, the modulation techniques may be combined where the one or more control modules 500 modulate the visible light L generated by the visible light source 48 based on more than one modulation technique. For example, the visible light L may be modulated based on polarization and intensity.

The visible light source 48 is any type of light-emitting device configured to provide a constant source of illumination as the one or more control modules 500 modulate the visible light L. That is, the visible light L generated by the visible light source 48 appears constant when viewed by the human eye, although the visible light source 48 is being modulated to transmit data. The visible light source 48 includes an array of light-emitting elements 554. In one non-limiting embodiment, the light-emitting elements 554 are LEDs or laser diodes.

In one embodiment, each light-emitting element 554 of the visible light source 48 emits light at the same wavelength spectrum. For example, in one non-limiting embodiment, each light-emitting element 554 that is part of the visible light source 48 emits the visible light L at a germicidal wavelength spectrum ranging from about 405 to about 470 nanometers to create blue light. In this embodiment, the visible light L sanitizes the conditioned air 36 flowing through the air duct 40. As another example, in one embodiment each light-emitting element 554 that is part of the visible light source 48 is a white LED. Alternatively, in another embodiment, two or more light-emitting elements 554 that are part of the visible light source 48 emit the visible light L at different wavelength spectrums. The visible light L emitted by light-emitting elements 554 at the different wavelength spectrums are combined to create the visible light L at a single wavelength spectrum. For example, in one embodiment, the light-emitting elements 554 are red, green, and blue (RGB) LEDs that emit visible light at different wavelength spectrums to create red, blue, and green light. The visible light L emitted at different wavelength spectrums by the RGB LEDs are combined to create the visible light L, where the visible light L is within the white light spectrum. As another example, the visible light L emitted by the RGB LEDs are combined to create blue light.

In another embodiment, two or more of the light-emitting elements 554 emit the visible light L at two or more unique wavelength spectrums, however, it is to be appreciated that the visible light L at the two or more unique wavelength spectrums are not combined. Instead, each unique wavelength spectrum conveys a unique set of data to one or more portable electronic devices 510 located within the interior cabin 58 of the aircraft 10 (FIG. 1). For example, in one non-limiting embodiment, each light-emitting element 554 that is part of the visible light source 48 may represent an LED that emits light at a unique wavelength spectrum. The one or more control modules 500 modulate the light-emitting elements 554 individually based on their unique wavelength spectrum, thereby creating the unique set of data. In the present example, each portable electronic device 510 located within the interior cabin 58 corresponds to one of the unique wavelength spectrums emitted by the light-emitting elements 554 of the visible light source 48. Thus, the visible light source 48 may be used to provide a unique set of data to each of the portable electronic devices 510.

The visible light L impinges against the reflective inner surface 46 of the air duct 40, where a portion of the visible light L generated by the visible light source 48 exits the air duct 40 through the lighting apertures 72 disposed along the main body 42 of the air duct 40. As mentioned above, in one embodiment the lighting apertures 72 each represent the overhead light for a passenger 570 located within the interior cabin 58 of the aircraft 10 (FIG. 1) and replace a traditional lamp that is used to provide visible light to passengers 570. As seen in FIG. 11, the visible light L exiting the the lighting apertures 72 is transmitted to one or more of the portable electronic devices 510, which are located outside of the air duct 40.

Figure 12:
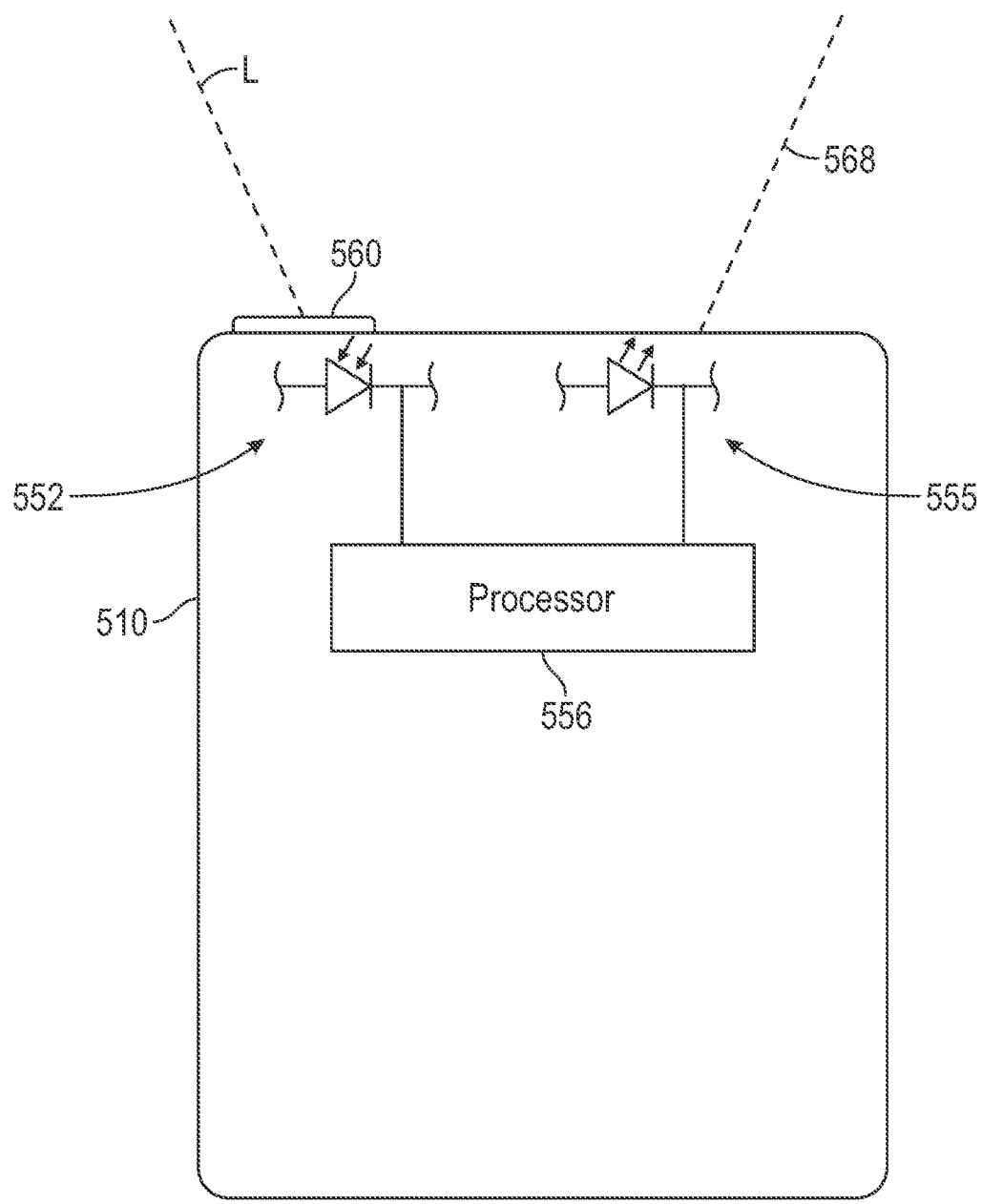
FIG. 12 is a schematic diagram of one of the electronic devices shown in FIG. 11, according to an exemplary embodiment.

FIG. 12 is a schematic diagram of one of the portable electronic devices 510 shown in FIG. 11. The portable electronic devices 510 each include an optical receiver 552, an optical transmitter 555, and one or more processors 556, where the one or more processors 556 are in electronic communication with the optical receiver 552 and the optical transmitter 555. In one embodiment, the portable electronic devices 510 represent personal electronic devices that are carried by the passengers 570 of the aircraft 10 (FIG. 1) such as, but are not limited to, laptops, smartphones, and smartwatches. Referring to FIGS. 11 and 12, the optical receiver 552 of the portable electronic device 510 detects the visible light L that exits the air duct 40 through the lighting apertures 72 and converts the visible light L into a readable electrical data signal that is transmitted to the one or more processors 556. The optical receiver 552 is any type of device that converts visible light into readable electrical data signal such as, for example, a photodiode.

As mentioned above, in one embodiment, the light-emitting elements 554 emit the visible light L at two or more unique wavelength spectrums, where each unique wavelength spectrum corresponds to one of the portable electronic devices 510. Referring specifically to FIG. 12, in one embodiment each portable electronic device 510 includes a light filter 560 (shown in FIG. 12) that allows light emitted at the unique wavelength spectrum corresponding to a particular portable electronic device 510 to pass and reach the optical receiver 552. Referring to both FIGS. 11 and 12, in one example the portable electronic device 510A may include a light filter 560 that allows light emitted at the corresponding unique wavelength spectrum ranging from about 620 to about 750 nanometers (red light), the portable electronic device 510B may include a light filter 560 that allows light emitted at the corresponding unique wavelength spectrum ranging from about 405 to about 440 nanometers (blue light), and the portable electronic device 510C may include a light filter 560 that allows light emitted at the corresponding unique wavelength spectrum ranging from about 500 to about 565 nanometers (green light).

In one embodiment, one-way communication is established between the portable electronic devices 510 and the air duct system 20, where the visible light source 48 that is part of the air duct system 20 transmits data to the portable electronic device 510 based on a visible light communication protocol. In another embodiment, two-way communication may be established between the portable electronic devices 510 and a receiver 562 for the aircraft 10 (FIG. 1) that is part of the air duct system 20, where one or more of the portable electronic devices 510 transmit data to the receiver 562. As explained below, the receiver 562 is configured to receive radio frequency waves 564 that are generated based on light 568. Specifically, the light 568 is generated by the optical transmitter 555 of one of the portable electronic devices 510 (shown in FIG. 12). The optical transmitter 555 converts the readable electrical data signals received from the one or more processors 556 of the portable electronic device 510 into the light 568. It is to be appreciated that the light 568 is undetectable to the human eye. The light 568 is either infrared light or, in the alternative, the light 568 is low-intensity visible light that is undetectable to the human eye and includes an irradiance of less than ten Watts/meter$^2$. The optical transmitter 555 is any type of device that converts the readable electrical data signal into infrared or visible light such as, for example, an infrared LED or white LED.

The air duct system 20 also includes one or more antennas 578 that each correspond to one of the photovoltaic devices 576. Each photovoltaic device 576 is in electronic communication with a corresponding antenna 578. It is to be appreciated that the photovoltaic device 576 generates electricity based on infrared light, visible light, or both infrared and visible light, depending on the light 568 emitted by the optical transmitter 555 of the portable electronic devices 510. The corresponding antenna 578 is located within the passageway 44 of the air duct 40. A portion of the light 568 generated by the optical transmitter 555 of one of the portable electronic devices 510 (shown in FIG. 12) impinges against one of the photovoltaic devices 576, where the photovoltaic device 576 converts the light 568 into a modulated electric current that drives the corresponding antenna 578 to create the radio frequency waves 564. The radio frequency waves 564 are directed along the reflective inner surface 46 of the air duct 40. The radio frequency waves 564 impinge against the reflective inner surface 46 of the air duct 40 and are intercepted by the receiver 562. The receiver 562 then converts the radio frequency waves 564 into a readable electrical data signal.

The receiver 562 is positioned within the passageway 44 of the air duct 40 to intercept the radio frequency waves 564 that impinge against the reflective inner surface 46 of the air duct 40. Specifically, in the example as shown in FIG. 11, the receiver 562 is positioned at the end 50 of the air duct 40 situated at the front end 52 of the aircraft 10 (FIG. 1). However, it is to be appreciated that the position of the receiver 562 is not limited to the position shown in FIG. 11 so long as the receiver 562 is positioned to intercept the radio frequency waves 564.

Figure 13:
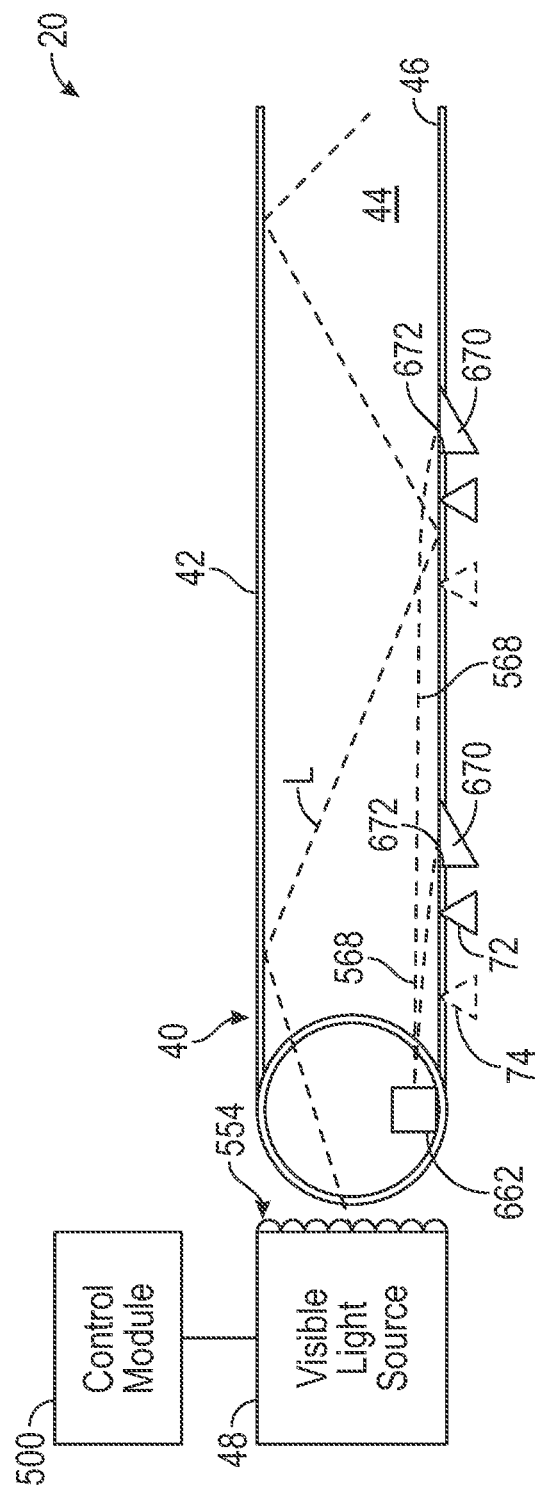
FIG. 13 is an alternative embodiment of the air duct system shown in FIG. 11, according to an exemplary embodiment.

FIG. 13 is an alternative embodiment of the air duct system 20 shown in FIG. 11, where the or more photovoltaic devices 576 and the corresponding antennas 578 are replaced one or more light-transmitting elements 670. Each light-transmitting element 670 is placed within a corresponding aperture 672 disposed along the main body 42 of the air duct 40. The light-transmitting elements 670 each represent optical elements that change a direction of travel of at least a portion of the light 568 that strikes. The mechanism for the changing the direction of travel of at least a portion of the light 568 is created by refraction, diffraction, scattering, or any combination thereof. Also, the receiver 562 is replaced by an optical receiver 662 disposed within the passageway 44 of the air duct 40. A portion of the light 568 generated by the optical transmitter 555 enters the air duct 40 through one or more of the light-transmitting elements 670. As seen in FIG. 13, the light-transmitting elements 670 are each configured to direct at least a portion of the light 568 towards the optical receiver 662 that is disposed within the passageway 44 of the air duct 40. The optical receiver 662 that is part of the air duct 40 converts the converts the light 568 into a readable electrical data signal.

Figure 14A:
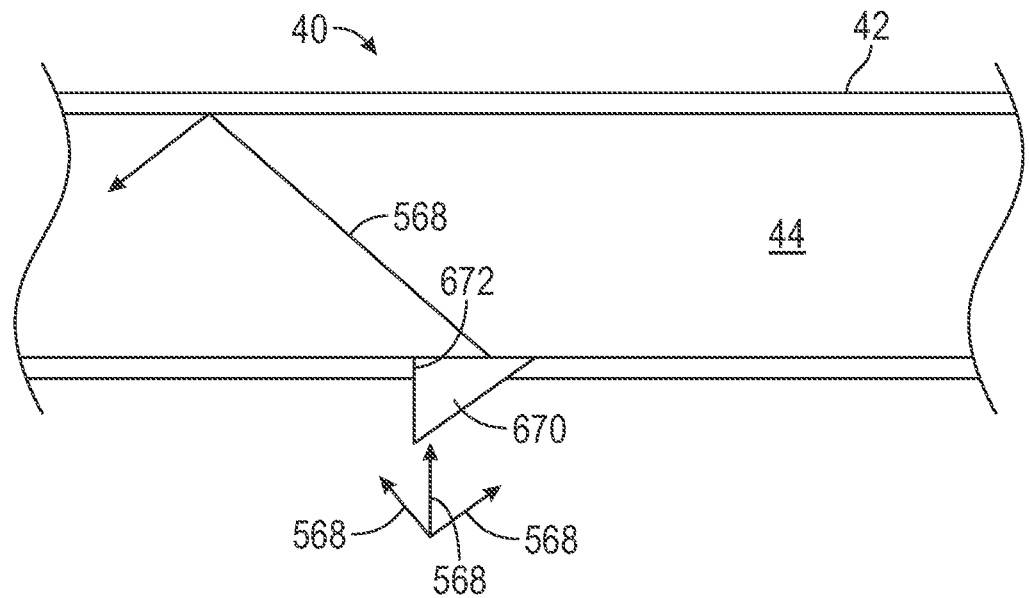
FIG. 14A illustrates one embodiment of a light-transmitting element shown in FIG. 13, according to an exemplary embodiment.
Figure 14B:
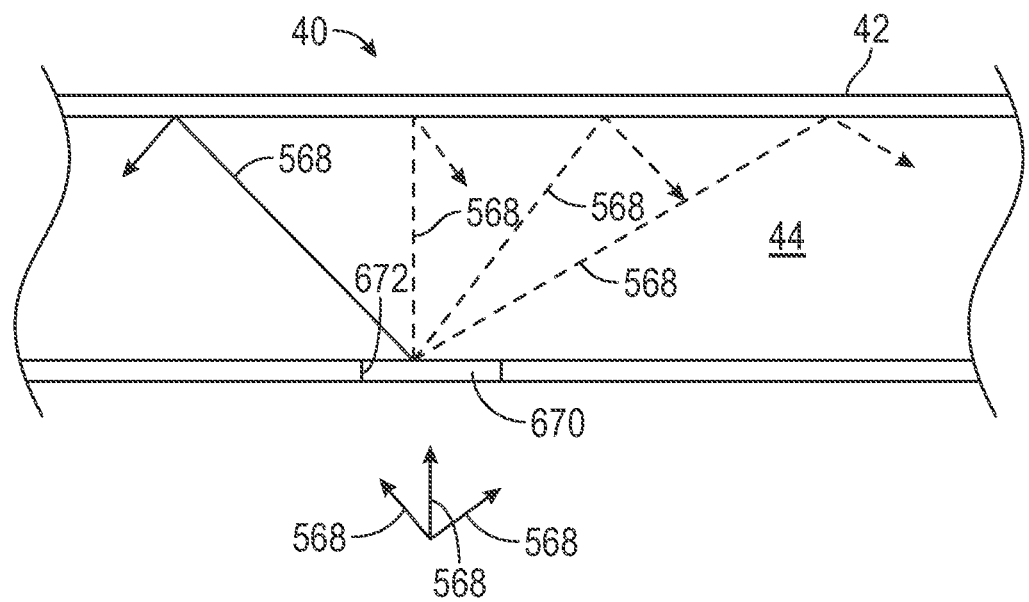
FIG. 14B illustrates another embodiment of the light-transmitting element shown in FIG. 13, according to an exemplary embodiment.

The light-transmitting element 670 is illustrated in FIGS. 14A and 14B. In the embodiment as shown in FIGS. 13 and 14A, the light-transmitting element 670 is a prism that redirects a majority of the light 568 generated by the optical transmitter 555 towards the optical receiver 662. In the embodiment as shown in FIG. 14B, the light-transmitting element 670 is a light-diffusing device that disperses the light 568 throughout the passageway 44 of the air duct 40, where a portion of the light 568 dispersed throughout the passageway 44 of the air duct 40 is directed towards the optical receiver 662. Some examples of light-scattering devices include, but are not limited to, a translucent pane, a micro-lens array, and a diffraction grating. The translucent pane may be, for example, frosted glass.

Figure 15:
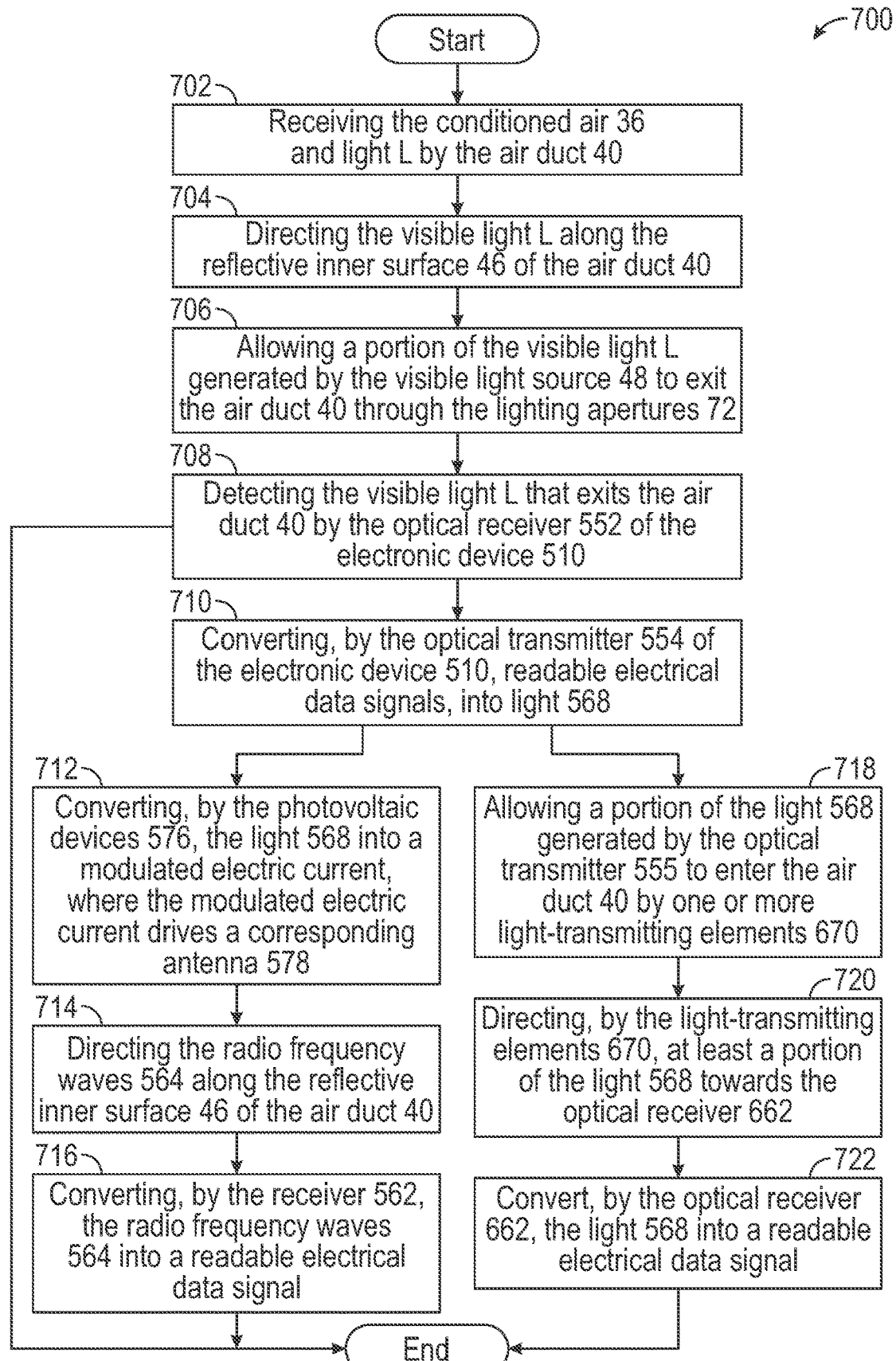
FIG. 15 is a process flow diagram illustrating a method for transmitting air, visible light, and the data through the air duct shown in FIGS. 11 and 13, according to an exemplary embodiment.

FIG. 15 is a process flow diagram illustrating a method 700 of transmitting air, visible light, and the data through the air duct 40 of the aircraft 10. Referring to FIGS. 11-15, the method 700 begins at block 702. In block 702, the air duct 40 receives the conditioned air 36 and visible light L. As mentioned above, the one or more control modules 500 instruct the visible light source 48 to modulate the visible light L based on a visible light communication protocol, where the visible light is a medium for transmitting data. The method 700 may then proceed to block 704.

In block 704, the visible light L is directed along the reflective inner surface 46 of the air duct 40, where the visible light L reflects off the reflective inner surface 46 and travels along the passageway 44 of the air duct 40. The method 700 may then proceed to block 706.

In block 706, a portion of the visible light L generated by the visible light source 48 is allowed to exit the air duct 40 through the lighting apertures 72 disposed along the main body 42 of the air duct 40. The method 700 may then proceed to block 708.

In block 708, the optical receiver 552 of the portable electronic device 510 (FIG. 12) detects the visible light L that exits the air duct 40 through the lighting apertures 72 and converts the visible light L into a readable electrical data signal that is transmitted to the one or more processors 556. In one embodiment, the method 700 may then terminate. However, if two-way communication is established between the portable electronic devices 510 and a receiver 562 for the aircraft 10 (FIG. 1) then the method 700 may proceed to block 710.

In block 710, the optical transmitter 555 of the portable electronic device 510 (FIG. 12) converts the readable electrical data signals received from the one or more processors 556 of the portable electronic device 510 into the light 568. The method 700 may then proceed to block 712 if the embodiment shown in FIG. 11 with the photovoltaic devices 576 and the corresponding antennas 578 is employed by the air duct system 20. The method 700 proceeds to block 718 if the embodiment shown in FIG. 13 with one or more light-transmitting elements 670 is employed.

In block 712, a portion of the light 568 generated by the optical transmitter 555 of one of the portable electronic devices 510 (shown in FIG. 12) is converted into a modulated electric current by one or more photovoltaic devices 576, where the modulated electric current drives the corresponding antenna 578 to create the radio frequency waves 564. As mentioned above, the antennas 578 are located within the passageway 44 of the air duct 40. The method 700 may then proceed to block 714.

In block 714, the radio frequency waves 564 are directed along the reflective inner surface 46 of the air duct 40, where the radio frequency waves 564 impinge against the reflective inner surface 46 of the air duct 40 and are intercepted by the receiver 562. The method 700 may then proceed to block 716.

In block 716, the receiver 562 then converts the radio frequency waves 564 into a readable electrical data signal. As mentioned above and shown in FIG. 11, the receiver 562 is positioned within the passageway 44 of the air duct 40. The method 700 may then terminate or return to block 702.

As mentioned above, the method 700 proceeds to block 718 if the embodiment shown in FIG. 13 with one or more light-transmitting elements 670 is employed. In block 718, one or more of the light-transmitting elements 670 (FIGS. 13, 14A, and 14B) allow a portion of the light 568 generated by the optical transmitter 555 of one of the portable electronic devices 510 (shown in FIG. 12) to enter the air duct 40. Each light-transmitting element 670 is placed within a corresponding aperture 672 disposed along the main body 42 of the air duct 40. The method 700 may then proceed to block 720.

In block 720, the light-transmitting elements 670 direct at least a portion of the light 568 towards the optical receiver 662 that is disposed within the passageway 44 of the air duct 40. The method 700 may then proceed to block 722.

In block 722, the optical receiver 662 converts the light 568 into a readable electrical data signal. The method 700 may then terminate or return to block 702.

Figure 17:
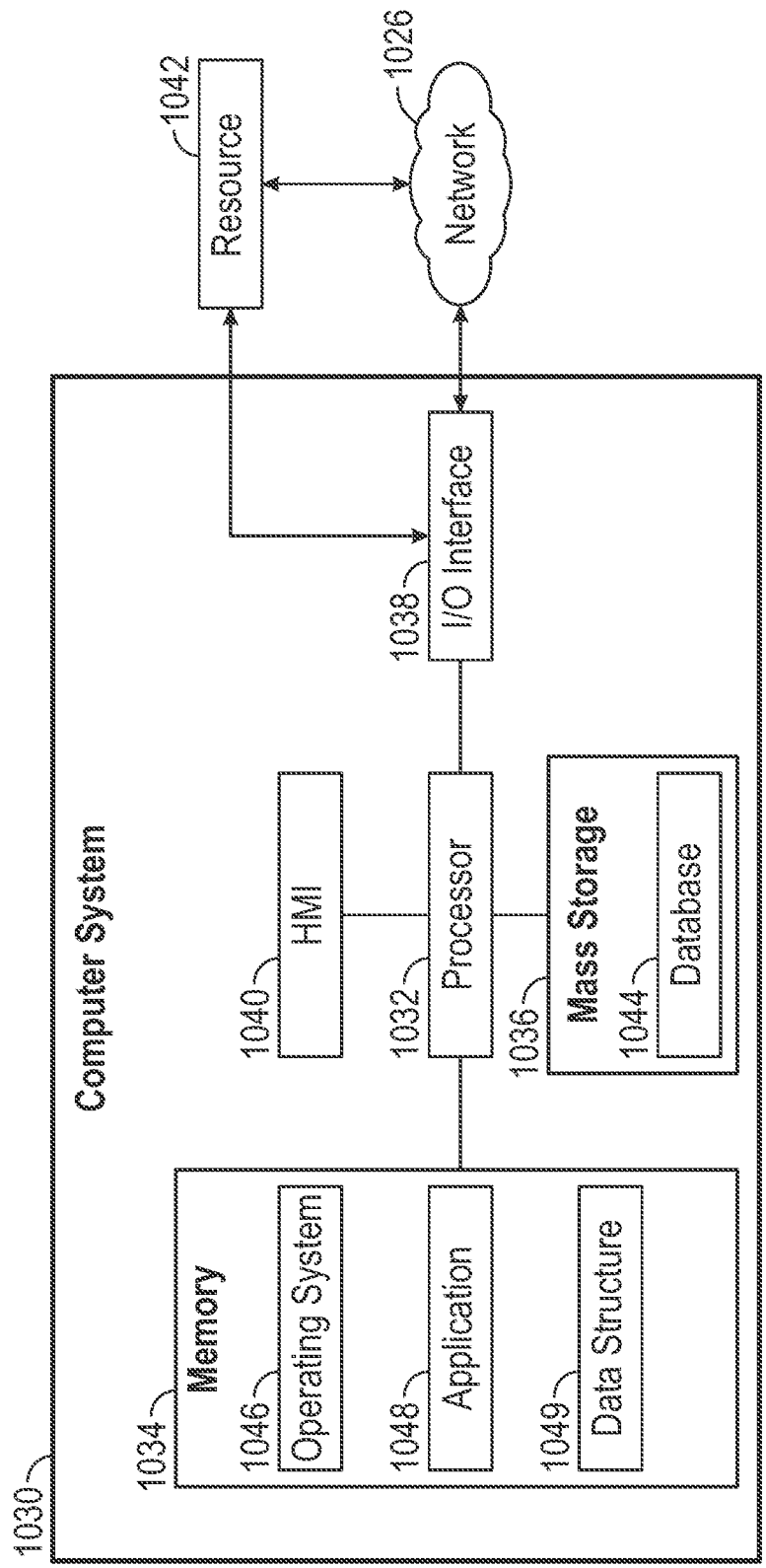
FIG. 17 is an illustration of a computer system for the control module shown in FIGS. 11 and 13, according to an exemplary embodiment.

FIG. 17 is a schematic diagram of an embodiment of the air duct system 20 for transmitting visible light, electrical power, and data, where the visible light L is emitted at the germicidal wavelength spectrum to create blue light. Accordingly, in the embodiment as shown in FIG. 17, the air duct system 20 simultaneously transmits the visible light L, electrical power, data, and sanitizes the conditioned air 36 flowing through the air duct 40. As explained below, the air duct system 20 may provide visible light L to aid a passenger in viewing their surroundings. The air duct system 20 may also provide a passenger with electrical power to power their portable electronic device 510, data to receive information from the internet, and sanitized air for the passenger to breathe. In the embodiment as shown in FIG. 17, a separate wall 800 is positioned between the air duct 40 and the interior cabin 58 of the aircraft 10 (FIG. 1). The wall 800 may represent a ceiling panel that is part of the interior cabin 58.

The visible light L generated by the visible light source 48, which is blue light, impinges against the reflective inner surface 46 of the air duct 40, where a first portion 802 of the visible light L exits the air duct 40 through one of the corresponding apertures 672 that contain a light-transmitting element 670. The light-transmitting element 670 directs the first portion 802 of the visible light L into the interior cabin 58 of the aircraft 10. As explained below, the first portion 802 of the visible light L provides data to one or more portable electronic devices 510 located in the interior cabin 58 and is also used to provide illumination in the interior cabin 58. As seen in FIG. 17, one or more photovoltaic devices 76 are disposed along the reflective inner surface 46 of the air duct 40. Each of the one or more photovoltaic devices 76 disposed along the reflective inner surface 46 of the air duct 40 are electrically connected and provide electrical power to a corresponding electronic device 78 by an electrical connection 806. As mentioned above, the electronic devices 78 correspond to individual electronic devices for each passenger within the aircraft 10. A second portion 804 of the visible light L impinges against one of the photovoltaic devices 76 and is converted into the electrical power provided to the corresponding electronic device 78.

Figure 16:
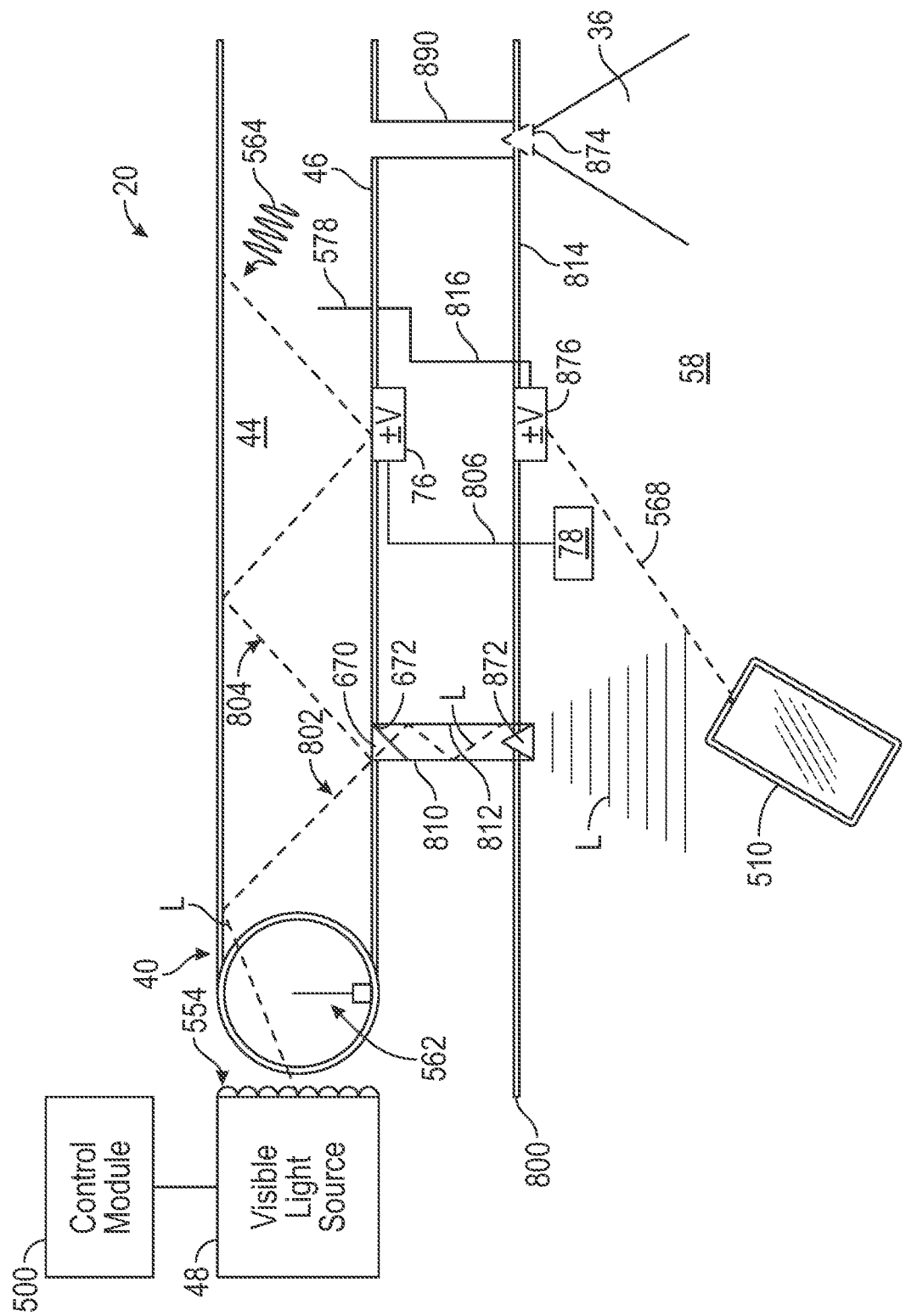
FIG. 16 illustrates another embodiment of the air duct system shown in FIG. 11 for transmitting visible light, data, electrical power, and sanitized air.

Continuing to refer to FIG. 16, the air duct system 20 also includes a light-reflecting pipe 810. The light-reflecting pipe 810 includes a reflective inner surface 812. As seen in FIG. 16, the light-reflecting pipe 810 is disposed between the light-transmitting element 670 that is part of the air duct 40 and a corresponding light aperture 872 that is disposed along the wall 800. As mentioned above, the light aperture 872 represents the overhead light for a passenger located within the interior cabin 58 and replaces a traditional lamp provided to passengers. The first portion 802 of the visible light L exits the air duct 40 through one of the corresponding apertures 672 that contain a light-transmitting element 670, impinges against the reflective inner surface 812 of the light-reflecting pipe 810, and enters the interior cabin 58 through the light aperture 872. Accordingly, the first portion 802 of the visible light L provides data to one or more portable electronic devices 510 as well as visible light L to the passengers located within the interior cabin 58.

In an embodiment, two-way communication is established between the portable electronic devices 510 and the receiver 562 of the aircraft 10 (FIG. 1). The air duct system 20 includes one or more photovoltaic devices 876 disposed along a lower surface 814 of the wall 800, where the lower surface 814 of the wall is located within the interior cabin 58 of the aircraft 10. An electrical connection 816 is provided between one of the photovoltaic devices 876 located within the interior cabin 58 and the corresponding antenna 578 located within the passageway 44 of the air duct system 20.

Referring to both FIGS. 12 and 16, in an embodiment where two-way communication is established between one of the portable electronic devices 510 and the receiver 562 of the aircraft 10 (FIG. 1), the light 568 is transmitted by the optical transmitter 555 of one of the portable electronic devices 510 (FIG. 12). As mentioned above, the light 568 may be infrared light or low-intensity visible light. A portion of the light 568 generated by the optical transmitter 555 of one of the portable electronic devices 510 (shown in FIG. 12) impinges against the photovoltaic devices 876, where the photovoltaic device 876 converts the light 568 into a modulated electric current that drives the corresponding antenna 578 to create the radio frequency waves 564. The radio frequency waves 564 are directed along the reflective inner surface 46 of the air duct 40. The radio frequency waves 564 impinge against the reflective inner surface 46 of the air duct 40 and are intercepted by the receiver 562. The receiver 562 then converts the radio frequency waves 564 into a readable electrical data signal.

The air duct system 20 also includes a pipe 890 that fluidly connects the passageway 44 of the air duct 40 with a corresponding air valve 874 disposed along the wall 800. The air valve 874 releases the conditioned air 36 into the interior cabin 58. The conditioned air 36 travels through the passageway 44 of the air duct 40, through the pipe 890, and is released into the interior cabin 58 through the air valve 874. As mentioned above, the conditioned air 36 has been sanitized by the the visible light L, which is emitted at the germicidal wavelength spectrum to create blue light.

Referring to FIGS. 11-16, the disclosed air duct system provides various technical effects and benefits. Specifically, the air duct system provides passengers with light, data, electrical power, and sanitized air, and therefore simultaneously achieves four functions for improving the flying experience. First, a portion of the visible light transmitted by the air duct of the air duct system illuminates the interior cabin of the aircraft to improve visibility. Second, by modulating the visible light, the air duct system transmits data that is received by a personal electronic device of a passenger. Third, a portion of the visible light is converted to electrical power that powers an electronic device. Fourth, in embodiments, the visible light is emitted at a germicidal wavelength spectrum to create blue light, thereby sanitizing the conditioned air that flows through the air duct.

Referring to FIG. 17, the one or more control modules may be implemented on one or more computer devices or systems, such as exemplary computer system 1030. The computer system 1030 includes a processor 1032, a memory 1034, a mass storage memory device 1036, an input/output (I/O) interface 1038, and a Human Machine Interface (HMI) 1040. The computer system 1030 is operatively coupled to one or more external resources 1042 via the network 1026 or I/O interface 1038. External resources may include, but are not limited to, servers, databases, mass storage devices, peripheral devices, cloud-based network services, or any other suitable computer resource that may be used by the computer system 1030.

The processor 1032 includes one or more devices selected from microprocessors, micro-controllers, digital signal processors, microcomputers, central processing units, field programmable gate arrays, programmable logic devices, state machines, logic circuits, analog circuits, digital circuits, or any other devices that manipulate signals (analog or digital) based on operational instructions that are stored in the memory 1034. Memory 1034 includes a single memory device or a plurality of memory devices including, but not limited to, read-only memory (ROM), random access memory (RAM), volatile memory, non-volatile memory, static random-access memory (SRAM), dynamic random-access memory (DRAM), flash memory, cache memory, or any other device capable of storing information. The mass storage memory device 1036 includes data storage devices such as a hard drive, optical drive, tape drive, volatile or non-volatile solid-state device, or any other device capable of storing information.

The processor 1032 operates under the control of an operating system 1046 that resides in memory 1034. The operating system 1046 manages computer resources so that computer program code embodied as one or more computer software applications, such as an application 1048 residing in memory 1034, may have instructions executed by the processor 1032. In an alternative example, the processor 1032 may execute the application 1048 directly, in which case the operating system 1046 may be omitted. One or more data structures 1049 also reside in memory 1034, and may be used by the processor 1032, operating system 1046, or application 1048 to store or manipulate data.

The I/O interface 1038 provides a machine interface that operatively couples the processor 1032 to other devices and systems, such as the network 1026 or external resource 1042. The application 1048 thereby works cooperatively with the network 1026 or external resource 1042 by communicating via the I/O interface 1038 to provide the various features, functions, applications, processes, or modules comprising examples of the disclosure. The application 1048 also includes program code that is executed by one or more external resources 1042, or otherwise rely on functions or signals provided by other system or network components external to the computer system 1030. Indeed, given the nearly endless hardware and software configurations possible, persons having ordinary skill in the art will understand that examples of the disclosure may include applications that are located externally to the computer system 1030, distributed among multiple computers or other external resources 1042, or provided by computing resources (hardware and software) that are provided as a service over the network 1026, such as a cloud computing service.

The HMI 1040 is operatively coupled to the processor 1032 of computer system 1030 in a known manner to allow a user to interact directly with the computer system 1030. The HMI 1040 may include video or alphanumeric displays, a touch screen, a speaker, and any other suitable audio and visual indicators capable of providing data to the user. The HMI 1040 also includes input devices and controls such as an alphanumeric keyboard, a pointing device, keypads, pushbuttons, control knobs, microphones, etc., capable of accepting commands or input from the user and transmitting the entered input to the processor 1032.

A database 1044 may reside on the mass storage memory device 1036 and may be used to collect and organize data used by the various systems and modules described herein. The database 1044 may include data and supporting data structures that store and organize the data. In particular, the database 1044 may be arranged with any database organization or structure including, but not limited to, a relational database, a hierarchical database, a network database, or combinations thereof. A database management system in the form of a computer software application executing as instructions on the processor 1032 may be used to access the information or data stored in records of the database 1044 in response to a query, where a query may be dynamically determined and executed by the operating system 1046, other applications 1048, or one or more modules.

The description of the present disclosure is merely exemplary in nature and variations that do not depart from the gist of the present disclosure are intended to be within the scope of the present disclosure. Such variations are not to be regarded as a departure from the spirit and scope of the present disclosure.

What is claimed is:

1. An air duct system, comprising:
   an air duct having a main body, wherein the main body of the air duct defines a passageway having a reflective inner surface;
   a visible light source configured to generate visible light, wherein the visible light source directs the visible light along the reflective inner surface of the air duct; and
   one or more control modules in electronic communication with the visible light source, wherein the one or more control modules instruct the visible light source to modulate the visible light based on a visible light communication protocol, and wherein the visible light is a medium for transmitting data.

2. The air duct system of claim 1, wherein the visible light communication protocol is the light fidelity standard as set forth by the Institute of Electrical and Electronics Engineers (IEEE) 802.11 family of standards.

3. The air duct system of claim 1, wherein the one or more control modules modulate the visible light generated by the visible light source based on one or more of the following modulation techniques: frequency modulation, intensity modulation, and polarization modulation.

4. The air duct system of claim 1, wherein the visible light source includes an array of light-emitting elements.

5. The air duct system of claim 4, wherein each light-emitting element that is part of the visible light source emits light at the same wavelength spectrum.

6. The air duct system of claim 1, wherein the visible light source emits the visible light at a germicidal wavelength spectrum ranging from about 405 to about 470 nanometers to create blue light.

7. The air duct system of claim 1, comprising:
   one or more light-transmitting elements, wherein each light-transmitting element is placed within a corresponding aperture disposed along the main body of the air duct, and wherein a first portion of the visible light exits the air duct through one of the corresponding apertures to provide the data.

8. The air duct system of claim 7, comprising:
   one or more photovoltaic devices disposed along the reflective inner surface of the air duct; and
   one or more corresponding electronic devices that are each electrically connected to one of the one or more photovoltaic devices, wherein a second portion of the visible light impinges against one of the one or more photovoltaic devices and is converted into electrical power provided to one of the corresponding electronic devices.

9. The air duct system of claim 1, comprising:
   one or more photovoltaic devices disposed along an outer surface of the air duct; and
   one or more antennas, wherein each photovoltaic device is in electronic communication with a corresponding antenna and the one or more antennas are located within the passageway of the air duct.

10. The air duct system of claim 9, wherein the one or more photovoltaic devices generate electricity based on one of the following: infrared light and visible light.

11. The air duct system of claim 9, wherein the one or more photovoltaic devices convert light into a modulated electric current that drives the corresponding antenna to create radio frequency waves.

12. The air duct system of claim 11, comprising:
   a receiver positioned within the passageway of the air duct, wherein the receiver intercepts the radio frequency waves.

13. The air duct system of claim 1, comprising:
   one or more light-transmitting elements, wherein each light-transmitting element is placed within a corresponding aperture disposed along the main body of the air duct.

14. The air duct system of claim 13, wherein the one or more light-transmitting elements are one or more of the following: a prism, a translucent pane, a micro-lens array, and a diffraction grating.

15. An aircraft, comprising:
   an air duct system, comprising:
      an air duct having a main body, wherein the main body of the air duct defines a passageway having a reflective inner surface;
      a visible light source configured to generate visible light, wherein the visible light source directs the visible light along the reflective inner surface of the air duct;
      one or more control modules in electronic communication with the visible light source, wherein the one or more control modules instruct the visible light source to modulate the visible light based on a visible light communication protocol, and wherein the visible light is a medium for transmitting data;
      one or more light-transmitting elements, wherein each light-transmitting element is placed within a corresponding aperture disposed along the main body of the air duct, and wherein a first portion of the visible light exits the air duct through one of the corresponding apertures to provide the data;
      one or more photovoltaic devices disposed along the reflective inner surface of the air duct; and
      one or more corresponding electronic devices that are each electrically connected to one of the one or more photovoltaic devices, wherein a second portion of the visible light impinges against one of the one or more photovoltaic devices and is converted into electrical power provided to one of the corresponding electronic devices.

16. The aircraft of claim 15, wherein the visible light source emits the visible light at a germicidal wavelength spectrum ranging from about 405 to about 470 nanometers to create blue light.

17. A method for transmitting air, visible light, and data through an air duct of an aircraft, the method comprising:
- receiving, by the air duct, conditioned air and visible light, wherein a visible light source is modulated based on a visible light communication protocol by one or more control modules to generate the visible light;
- directing the visible light along a reflective inner surface of the air duct, wherein the visible light reflects off the reflective inner surface and travels along a passageway of the air duct; and
- allowing a portion of the visible light generated by the visible light source to exit the air duct through one or more lighting apertures disposed along a main body of the air duct.

18. The method of claim 17, comprising:
- detecting, by an optical receiver of a personal electronic device located in an interior cabin of the aircraft, the visible light exiting the air duct, wherein the optical receiver converts the visible light into a readable electrical data signal transmitted to one or more processors that are part of the personal electronic device; and
- converting, by an optical transmitter of the personal electronic device, readable electrical data signals received from the one or more processors of the personal electronic device into light.

19. The method of claim 18, comprising:
- converting, by a photovoltaic device disposed along an outer surface of the air duct, a portion of the light generated by the optical transmitter into a modulated electric current, wherein the modulated electric current drives a corresponding antenna to create radio frequency waves and the corresponding antenna is located within the passageway of the air duct; and
- converting, by a receiver disposed within the passageway of the air duct, the radio frequency waves into a readable electrical data signal.

20. The method of claim 18, comprising:
- allowing, by one or more light-transmitting elements, a portion of the light generated by the optical transmitter to to enter the air duct, wherein the one or more light-transmitting element are placed within a corresponding aperture disposed along the main body of the air duct;
- directing, by the one or more light-transmitting elements, at least a portion of the light towards an optical receiver disposed within the passageway of the air duct; and
- converting, by the optical receiver, the light into a readable electrical data signal.

* * * * *